US007541169B2

(12) United States Patent
Freimuth et al.

(10) Patent No.: US 7,541,169 B2
(45) Date of Patent: Jun. 2, 2009

(54) SULFOTRANSFERASE SEQUENCE VARIANTS

(75) Inventors: Robert R. Freimuth, Rochester, MN (US); Eric D. Wieben, Rochester, MN (US); Richard M. Weinshilboum, Rochester, MN (US)

(73) Assignee: Mayo Foundation for Medical Education and Research, Rochester, NY (US)

( * ) Notice: Subject to any disclaimer, the term of this patent is extended or adjusted under 35 U.S.C. 154(b) by 150 days.

(21) Appl. No.: 11/348,099

(22) Filed: Feb. 6, 2006

(65) Prior Publication Data

US 2006/0134684 A1 Jun. 22, 2006

Related U.S. Application Data

(63) Continuation of application No. 09/792,695, filed on Feb. 23, 2001, now Pat. No. 7,026,163.

(51) Int. Cl.
*C12N 9/10* (2006.01)
*C07H 21/04* (2006.01)
(52) U.S. Cl. ........................ 435/193; 536/23.2
(58) Field of Classification Search ............... 435/193; 536/23.2
See application file for complete search history.

(56) References Cited

U.S. PATENT DOCUMENTS

| 5,451,683 | A | 9/1995 | Barrett et al. ............. 548/302.7 |
| 5,733,729 | A | 3/1998 | Lipshutz et al. .................. 435/6 |
| 5,770,722 | A | 6/1998 | Lockhart et al. ............ 536/25.3 |
| 6,265,561 | B1 | 7/2001 | Weinshilboum et al. ... 536/23.2 |

FOREIGN PATENT DOCUMENTS

| WO | WO 98/20019 | 5/1998 |
| WO | WO 99/57318 | 11/1999 |
| WO | WO 99/64630 | 12/1999 |
| WO | WO 00/20605 | 4/2000 |

OTHER PUBLICATIONS

Weinshilboum et al (1997) The FASEB Journal, vol. 11, pp. 3-14.*
GenBank Accession No. U66036, (May 13, 1997), Her et al.
GenBank Accession No. AF186251, (May 31, 2000), Freimuth et al.
GenBank Accession No. AF186252, (May 31, 2000), Freimuth et al.
GenBank Accession No. AF186253, (May 31, 2000), Freimuth et al.
GenBank Accession No. AF186254, (May 31, 2000), Freimuth et al.
GenBank Accession No. AF186255, (May 31, 2000), Freimuth et al.
GenBank Accession No. AF186256, (May 31, 2000), Freimuth et al.
GenBank Accession No. AF186257, (May 31, 2000), Freimuth et al.
GenBank Accession No. AF186258, (May 31, 2000), Freimuth et al.
GenBank Accession No. AF186259, (May 31, 2000), Freimuth et al.
GenBank Accession No. AF186260, (May 31, 2000), Freimuth et al.
GenBank Accession No. AF186261, (May 31, 2000), Freimuth et al.
GenBank Accession No. AF186262, (May 31, 2000), Freimuth et al.

Campbell et al., "Human Liver Phenol Sulfotransferase: Assay Conditions, Biochemical Properties and Partial Purification of Isozymes of the Thermostable Form," *Biochem. Pharmacol.*, 1987, 36(9):1435-1446.
Cleland, "Computer Programmes for Processing Enzyme Kinetic Data," *Nature*, 1963, 198:463-465.
Freimuth et al., "Pharmacogenetics of Human Sulfotransferase (Sult) 1C1: Gene Cloning, Resequencing and Common Single Nucleotide Polymorphisms," *Clinical Pharmacology & Therapeutics*, 2000, 67(2):140.
Cote et al., "Generation of human monoclonal antibodies reactive with cellular antigens," *Proc. Natl. Acad. Sci. USA*, 1983, 80:2026-2030.
Hacia et al., "Detection of heterozygous mutations in *BRCA1* using high density oligonucleotide arrays and two-color fluorescence analysis," *Nat. Genet.*, 1996, 14:441-447.
Halushka et al., "Patterns of sinle-nucleotide polymorphisms in candidate genes for blood-pressure homeostasis," *Nat. Genet.*, 1999, 22:239-247.
Her et al., "Human Sulfotransferase SULT1C1: cDNA Cloning, Tissue-Specific Expression, and Chromosomal Localization," *Genomics*, 1997, 41:467-470.
Ho et al., "Site-directed mutagenesis by overlap extension using the polymerase chain reaction," *Gene*, 1989, 77:51-59.
Huse et al., "Generation of a Large Combinatorial Library of the Immunoglobulin Repertoire in Phage Lambda," *Science*, 1989, 246:1275-1281.
Hyrup and Nielsen, "Peptide Nucleid Acids (PNA): Synthesis, Properties and Potential Applications," *Bioorgan. Med. Chem.*, 1996, 4:5-23.
Myakishev et al., "High-Throughput SNP Genotyping by Allele-Specific PCR with Universal Energy-Transfer-Labeled Primers," *Genome Res.*, 2001, 11:163-169.
Prince et al., "Robust and Accurate Single Nucleotide Polymorphism Genotyping by Dynamic Allele-Specific Hybridization (DASH): Design Criteria and Assay Validation," *Genome Res.*, 2001, 11:152-162.
Sakakibara et al., "Molecular Cloning, Expression, and Characterization of Novel Human SULT1C Sulfotransferases That Catalyze the Sulfonation of *N*-Hydroxy-2-acetylaminofluorene," *J. Biol. Chem.*, 1998, 273(51):33929-33935.
Schafer and Hawkins, "DNA variation and the future of human genetics," *Nat. Biotechnol.*, 1998, 16:33-39.
Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.
Summerton and Weller, "Morpholino Antisense Oligomers: Design, Preparation, and Properties," *Antisense & Nucleic Acid Drug Development*, 1997, 7:187-195.
Terwilliger and Ott, *Handbook of Human Genetic Linkage*, The Johns Hopkins University Press, Baltimore and London, 1994, pp. 188-193.

(Continued)

*Primary Examiner*—Tekchand Saidha
(74) *Attorney, Agent, or Firm*—Fish & Richardson P.C.

(57) ABSTRACT

Isolated sulfotransferase nucleic acid molecules that include a nucleotide sequence variant and nucleotides flanking the sequence variant are described, as well as sulfotransferase allozymes. Methods for determining if a mammal is predisposed to thyroid disease or cancer also are described.

8 Claims, 13 Drawing Sheets

OTHER PUBLICATIONS

Underhill et al., "Detection of Numerous Y Chromosome Biallelic Polymorphisms by Denaturing High-Performance Liquid Chromatography," *Genome Res.*, 1997, 7(10):996-1005.

Van Loon et al., "Human Kidney Thiopurine Methyltransferase Photoaffinity Labeling with *S*-Adenosyl-L-Methionine," *Biochem. Pharmacol.*, 1992, 44(4):775-785.

Van Loon and Weinshilboum, "Thiopurine Methyltransferase Isozymes in Human Renal Tissue," *Drug Metab. Dispos.*, 1990, 18(5):632-638.

Wilkinson, "Statistical Estimations in Enzyme Kinetics," *Biochem. J.*, 1961, 80:324-332.

Wong et al., "Human GM-CSF: Molecular Cloning of the Complementary DNA and Purification of the Natural and Recombinant Proteins," *Science*, 1985, 228:810-815.

Wood et al., "Human Liver Thermolabile Phenol Sulfotransferase: cDNA Cloning, Expression and Characterization," *Biochem. Biophys. Res. Commun.*, 1994, 198(3):1119-1127.

Mehmann et al. (1994) Appl. Environ. Microbiol., vol. 60(9), pp. 3105-3111.

Mehmann (Sep. 23, 1994) GenBank accession X78089.

Iida et al., "Catalog of 320 single nucleotide polymorphisms (SNPs) in 20 quinone oxidoreductase and sulfotransferase genes," *J. Hum. Genet.*, 2001, 46:225-240.

\* cited by examiner

```
      TCCAGCCTGGGCAACAGGAGTGAAACACCATCTCAAAAAAAAAAAAAAAAAAGAAAAAAG
1201  ---------+---------+---------+---------+---------+---------+ 1260 (-1115)
      AGGTCGGACCCGTTGTCCTCACTTTGTGGTAGAGTTTTTTTTTTTTTTTTTCTTTTTTC

AAAGAAAAGAAAGTTCAATTTATTGGGAAAAAAAGAGCCCTTTGGAAACAAGGAGGAAG
1261  ---------+---------+---------+---------+---------+---------+ 1320 (-1055)
      TTTCTTTTTCTTTCAAGTTAAATAACCCTTTTTTTCTCGGGAAACCTTTGTTCCTCCTTC

AAGAAGTGTCGGCAAAGAAGCATTAGGAGGTTCAGGGTCAAAGAAGACAAGGAAAGCTTT
1321  ---------+---------+---------+---------+---------+---------+ 1380 (-995)
      TTCTTCACAGCCGTTTCTTCGTAATCCTCCAAGTCCCAGTTTCTTCTGTTCCTTTCGAAA

GGCAAGAAGGGCAGATGGGGTGCAGAATTATGCTTCAATTCCAGAAAGGAAAGCACTGGG
1381  ---------+---------+---------+---------+---------+---------+ 1440 (-935)
      CCGTTCTTCCCGTCTACCCCACGTCTTAATACGAAGTTAAGGTCTTTCCTTTCGTGACCC

GTAGATACAAGGTTGGGGCTGGCAGAAGAGTAGCAGTTCAGAGATCATTAACACTTGATC
1441  ---------+---------+---------+---------+---------+---------+ 1500 (-875)
      CATCTATGTTCCAACCCCGACCGTCTTCTCATCGTCAAGTCTCTAGTAATTGTGAACTAG
                                                           5' Flanking
      CATTTAATTTCCCAGGTAACCAAAGACACCATGGAATATAATCTGCCTCCACTAAAGTGT
1501  ---------+---------+---------+---------+---------+---------+ 1560 (-815)
      GTAAATTAAAGGGTCCATTGGTTTCTGTGGTACCTTATATTAGACGGAGGTGATTTCACA
                                                       -760      T→G
      ACCTTTTGTACAATAAGGCAAAGAAAAAATAAGTACACACCTAAGCTCTAGACTTTTGTT
1561  ---------+---------+---------+---------+---------+----(-)---+ 1620 (-755)
      TGGAAAACATGTTATTCCGTTTCTTTTTATTCATGTGTGGATTCGAGATCTGAAAACAA CTATCCTCTCTGCATTTTCGGTGTGGATGAATACAACTTGGGAAGAAAGGAAAGAAGAAC
1621  ---------+---------+---------+---------+---------+---------+ 1680 (-695)
      GATAGGAGAGACGTAAAAGCCACACCTACTTATGTTGAACCCTTCTTTCCTTTCTTCTTG CAGCAGTTTTAAGCACTTACTATTTGCTCTGCAAAGTGTATTCATCAACATTGTTGCTTT
1681  ---------+---------+---------+---------+---------+---------+ 1740 (-635)
      GTCGTCAAAATTCGTGAATGATAAACGAGACGTTTCACATAAGTAGTTGTAACAACGAAA CAATCTTAAAGCATGGATTGGAGACAGGCAGTATTACCCACACTTCATAGATGCAGAAAT
1741  ---------+---------+---------+---------+---------+---------+ 1800 (-575)
      GTTAGAATTTCGTACCTAACCTCTGTCCGTCATAATGGGTGTGAAGTATCTACGTCTTTA
                      -547    A→G                      -518    C→T
      TAAATCTCAGGCTAAGGAGGAAGGAAAAGGGAGTTCACCAAATAAGCAGGAGCCTACCTG
1801  ---------+---------+------(-)-+---------+---------+------(-)+ 1860 (-515)
      ATTTAGAGTCCGATTCCTCCTTCCTTTTCCCTCAAGTGGTTTATTCGTCCTCGGATGGAC
```

FIG. 1A

```
                     -500   T→C
         AAGCCTGATGCATCTGGTCCTAGAGCCAACCTTCCATTTCCCCCCAGCCCCCACCTGTTT      5' Flanking
1861     ---------+---(-)---+---------+---------+---------+---------+ 1920 (-455)
         TTCGGACTACGTAGACCAGGATCTCGGTTGGAAGGTAAAGGGGGGTCGGGGGTGGACAAA AAGCTTCGAGGCCAGTGGGAGGAGGGAGGGGCCAGGCAGCTGAGGGCCAGGAAAGATGTG
1921     ---+---------+---------+---------+---------+---------+---------+ 1980 (-395)
         TTCGAAGCTCCGGTCACCCTCCTCCCTCCCCGGTCCGTCGACTCCCGGTCCTTTCTACAC AAAAACTCTAGCTGGTGACCGAGAGGAGGAGTAGAGTGTGCCCTTAGTTCATATGAACTA
1981     ---------+---------+---------+---------+---------+---------+ 2040 (-335)
         TTTTTGAGATCGACCACTGGCTCTCCTCCTCATCTCACACGGGAATCAAGTATACTTGAT GAGGGAGTTGGTATTTGCACAGCAGTCAGGGTCACATGAGTGATCATGGTACAGTGAGAA
2041     ---------+---------+---------+---------+---------+---------+ 2100 (-275)
         CTCCCTCAACCATAAACGTGTCGTCAGTCCCAGTGTACTCACTAGTACCATGTCACTCTT
                                  -258    C→T                                    Exon 1
         GTTCTCCCTCCCAGGGCCAGGTCACAGGGTTTGTTTCTGTTCAATCCGGATTCTTCCAGT
2101     ---------+-----(-)-+---------+---------+---------+---------+ 2160 (-215)
         CAAGAGGGAGGGTCCCGGTCCAGTGTCCCAAACAAAGACAAGTTAGGCCTAAGAAGGTCA
                                                       -176
         AAAAGCTTCAACTTCCCACACTGAAGCTGAGAGCCTCCCAAAGTGCTGGCTACCTGCTGA
2161     ---------+---------+---------+---------+---------+---------+ 2220 (-155)
         TTTTCGAAGTTGAAGGGTGTGACTTCGACTCTCGGAGGGTTTCACGACCGATGGACGACT
                   -149             C insertion
         GCGCCCCCGTAACTCTGACACAGTAGTAATTTGAGCCTCTGCAATTGCCGTCTGCTTCCT
2221     ------+---+---------+---------+---------+---------+---------+ 2280 (-95)
         CGCGGGGGCATTGAGACTGTGTCATCATTAAACTCGGAGACGTTAACGGCAGACGAAGGA GTGAAAGTCCTTTCCGTGCCCACTGACCCTTGAGTGGGCCTTTGAGCTGCTGACTTTCAG
2281     ---------+---------+---------+---------+---------+---------+ 2340 (-35)
         CACTTTCAGGAAAGGCACGGGTGACTGGGAACTCACCCGGAAACTCGACGACTGAAAGTC CTGGAACTTGAAGGTAAGAATATGGCTTAAAAGAAATTCTGTACCTAACTCGTTAATTTA
2341     ---------+---+-----+---------+---------+---------+--+------+ 2400
         GACCTTGAACTTCCATTCTTATACCGAATTTTCTTTAAGACATGGATTGAGCAATTAAAT
                                                         I1(37)  T→C
         TTTTTTAACCTTTAGCCACATAGGTGTGGCTTTACAGATGCATTTATTCAAACCAGAAAA
2401     ---------+---------+---------+---------+---------+---------+ 2460
         AAAAAATTGGAAATCGGTGTATCCACACCGAAATGTCTACGTAAATAAGTTTGGTCTTTT
                                                                          Intron 1
         GATCCTAAGAATCTGATAAAATAATATAAAAGAGTTTTGTTAACAGCCTCCAGCCTAAAA
2461     ---------+---------+---------+---------+---------+---------+ 2520
         CTAGGATTCTTAGACTATTTTATTATATTTTCTCAAAACAATTGTCGGAGGTCGGATTTT ATTCAGACCTAGAAATTCAGGACCCCCCTCAAATCACCTCCAAAAGCTCTCTCTCCTGTA
2521     ---------+---------+---------+---------+---------+---------+ 2580
         TAAGTCTGGATCTTTAAGTCCTGGGGGGAGTTTAGTGGAGGTTTTCGAGAGAGAGGACAT
```

FIG. 1A-1

```
        TTTCCCATAGGGACCCCAACCCTGAGACACTATGGCCCTGACCTCAGACCTGGGGAAACA
361     ---------+---------+---------+---------+---------+---------+ 420 (29)
        AAAGGGTATCCCTGGGGTTGGGACTCTGTGATACCGGGACTGGAGTCTGGACCCCTTTGT
                                                                                Exon 2
        GATAAAACTGAAAGAGGTGGAGGGGACCCTCCTGCAGCCTGCAACTGTGGACAACTGGAG
421     ---------+---------+---------+---------+---------+---------+ 480 (89)
        CTATTTTGACTTTCTCCACCTCCCCTGGGAGGACGTCGGACGTTGACACCTGTTGACCTC CCAGATCCAGAGCTTCGAGGCCAAACCAGATGATCTCCTCATCTGCACCTACCCTAAAGC
481     ---------+---------+---------+---------+---------+---------+ 540 (149)
        GGTCTAGGTCTCGAAGCTCCGGTTTGGTCTACTAGAGGAGTAGACGTGGATGGGATTTCG AGGTGATTGCAGGGTAGGAGGGACAGCAAAGACCTGCTGAGCCAGCACAGGCTCATCACT
541     ---------+---------+---------+---------+---------+---------+ 600
        TCCACTAACGTCCCATCCTCCCTGTCGTTTCTGGACGACTCGGTCGTGTCCGAGTAGTGA TAAGTTAGAATTCCCCTTCTTAGGAAACCTGCTCCTTCTTATTGTTCCACAATGGGTTTT
601     ---------+---------+---------+---------+---------+---------+ 660
        ATTCAATCTTAAGGGGAAGAATCCTTTGGACGAGGAAGAATAACAAGGTGTTACCCAAAA GGAGCTCAGGGCTCACACAGGATGCCTGATATCCGAGTTTTCCAGGAAAGCTGCTATGCT
661     ---------+---------+---------+---------+---------+---------+ 720
        CCTCGAGTCCCGAGTGTGTCCTACGGACTATAGGCTCAAAAGGTCCTTTCGACGATACGA       Intron 2

CTACCATGCACTGGTCTTGGGTGGAGAGACCCTTGCCTGTGCTGCTCCACTCCCTACAGA
721     ---------+---------+---------+---------+---------+---------+ 780
        GATGGTACGTGACCAGAACCCACCTCTCTGGGAACGGACACGACGAGGTGAGGGATGTCT

GATCCAAAGTCCATCCCTCATGGACTTCTATCACTCATGGCAAACAGGATTCTGACCCAA
781     ---------+---------+---------+---------+---------+---------+ 840
        CTAGGTTTCAGGTAGGGAGTACCTGAAGATAGTGAGTACCGTTTGTCCTAAGACTGGGTT

GGGGAGGGTGATGCAAACACCAAGGCTCTACATCCTCTTCGTTTACTCGGGACTCTTCAG
841     ---------+---------+---------+---------+---------+---------+ 900
        CCCCTCCCACTACGTTTGTGGTTCCGAGATGTAGGAGAAGCAAATGAGCCCTGAGAAGTC

GGAAGATTGTCTAACAGATTTCTGCTTCTCATCCTTCCTTTCTGAGCCTCAGGGACAACG
901     ---------+---------+---------+---------+---------+---------+ 960 (159)
        CCTTCTAACAGATTGTCTAAAGACGAAGAGTAGGAAGGAAAGACTCGGAGTCCCTGTTGC
                                 179   A→C                          215    G→A   Exon 3
        TGGATTCAGGAAATTGTGGATATGATTGAACAGAATGGGGACGTGGAGAAGTGCCAGCGA
961     ---------+---------+---------+---------+---------+---------+ 1020 (219)
        ACCTAAGTCCTTTAACACCTATACTAACTTGTCTTACCCCTGCACCTCTTCACGGTCGCT GCCATCATCCAACACCGCCATCCTTTCATTGAGTGGGCTCGGCCACCCCAACCTTCTGGT
1021    ---------+---------+---------+---------+---------+---------+ 1080
        CGGTAGTAGGTTGTGGCGGTAGGAAAGTAACTCACCCGAGCCGGTGGGGTTGGAAGACCA
```

FIG. 1B

```
        GAGAGCACCTCCCTCTTTCTCTCTTCCTGCTTTCTTTCCCTCTCTCTTCTGTTTTCCCCT
1081    ---------+---------+---------+---------+---------+---------+| 1140
        CTCTCGTGGAGGGAGAAAGAGAGAAGGACGAAAGAAAGGGAGAGAGAAGACAAAAGGGGA| I3(61-62)
                                                                      CT
        GTCTTTTCTCACTTTTCTCCTCTTCTCTCCTCTCTCTCTCCCCCA TCTCTCCTTCCTCTT   deletion
1141    ---------+---------+---------+---------+----|----+---------+ 1200
        CAGAAAAGAGTGAAAAGAGGAGAAGAGAGGAGAGAGAGAGGGGGT AGAGAGGAAGGAGAA
                                                    I3(107)          30 nucleotide
                                                                     deletion
        TTCTCTCTCCCTCCC TCTCTCCTTCCTCTTCTCTTTCTCTCTCATTTTCACTGTCATATG
1201    ---------+----|----+---------+---------+---------+---------+ 1260
        AAGAGAGAGGGAGGG AGAGAGGAAGGAGAAGAGAAAGAGAGAGTAAAAGTGACAGTATAC TTTCTTCCTTTTATCTTCCTCTCATCCTCTGTCTACATATTATTTAAGATTTTTTACCAA
1261    ---------+---------+---------+---------+---------+---------+ 1320
        AAAGAAGGAAAATAGAAGGAGAGTAGGAGACAGATGTATAATAAATTCTAAAAAATGGTT AAGTGAATCACCAAATGAAAAGGATGTGTGCTAGGGTCAGATTCTGCCTTATTTTCTTCT
1321    ---------+---------+---------+---------+---------+---------+ 1380
        TTCACTTAGTGGTTTACTTTTCCTACACACGATCCCAGTCTAAGACGGAATAAAAGAAGA TAAGCCCTCCCTCTGATCATGTGCAACTGTAGATCACATTGAAGATGTGAAAAACTGTAA
1381    ---------+---------+---------+---------+---------+---------+ 1440
        ATTCGGGAGGGAGACTAGTACACGTTGACATCTAGTGTAACTTCTACACTTTTTGACATT

GCCATTT
1441    -------1447
        CGGTAAA
```

FIG. 1B-1

```
      TGTTTTCAACTTTCTCTTTTATTCCTTTGCACTTTTTTTTGAGACAGGGTCTCACTCTGT
481 ---------+---------+---------+---------+---------+---------+ 540
      ACAAAAGTTGAAAGAGAAAATAAGGAAACGTGAAAAAAAACTCTGTCCCAGAGTGAGACA
                                                                                    Intron 3
      CACCCAGGCTAGAGTGCAGTAGTGCAAACACAGCTCACTGCAGCCTCAATTCT CTCGAGC
541 ---------+---------+---------+---------+---------+---+-----+ 600
      GTGGGTCCGATCTCACGTCATCACGTTTGTGTCGAGTGACGTCGGAGTTAAGA GAGCTCG
                                                                           I3(-2377)    T insertion
      TCAAGCGATCCTCCCATCTCAGCCTCCCGAGTAAGTAGCTGGGACTACAGGTGCGTATCA
601 ---------+---------+---------+---------+---------+---------+ 660
      AGTTCGCTAGGAGGGTAGAGTCGGAGGGCTCATTCATCGACCCTGATGTCCACGCATAGT CCATGCCCAGCTAATTTGGTATTTTTTTTTTAGAGACAGGATTTCACCATGTTGCCC
661 ---------+---------+---------+------+---+---------+---------+ 720
      GGTACGGGTCGATTAAAACCATAAAAAAAAAAATCTCTGTCCTAAAGTGGTACAACGGG
                                                                                    Exon 3b
      AGGCTGGTCTCAAACTCCTGAGCTCAAGCAATCCACCTGCCTCAACCTCCCAAAGTGCCA
721 ---------+---------+---------+---------+---------+---------+ 780
      TCCGACCAGAGTTTGAGGACTCGAGTTCGTTAGGTGGACGGAGTTGGAGGGTTTCACGGT AGATTACAGACGTGAGCCACTGCCCCTGGCTTCTTTGCATATTTAAACATAGTTATTT
781 --------+--+-----+---------+--+------+---------+---------+ 840
      TCTAATGTCTGCACTCGGTGACGGGGACCGGAAGAAACGTATAAAATTTGTATCAATAAA
                     I3(-2177) C→T   I3(-2118)   I3(-2158) C→T
      ATATTCTCTATTAGGTACCCAATAACTGAGGTCACTAGGGGTTTAGTTCTTCCACCTGTT
841 ---------+---------+---------+---------+---------+---------+ 900
      TATAAGAGATAATCCATGGGTTATTGACTCCAGTGATCCCCAAATCAAGAAGGTGGACAA
                                    I3(-2227)
      TTTTTTCTAGCTCTTGTTCATAGGGCTTTTCCCTCATTTGTTTTGTAATTTTGTATAAAA
901 ---------+---------+---------+---------+---------+---------+ 960
      AAAAAAGATCGAGAACAAGTATCCCGAAAAGGGAGTAAACAAAACATTAAAACATATTTT
                                                                                    Intron 3
      AGCTCTTTTCTCCCTGTCTTGATCTCACACCTACATTGGAACATTTCCAATCTAGAATAG
961 ---------+---------+---------+---------+---------+---------+ 1020
      TCGAGAAAAGAGGGACAGAACTAGAGTGTGGATGTAACCTTGTAAAGGTTAGATCTTATC TTTAAGTTAACTTCTGGTCCAAGCTGGTAGTATAATTTCATATCCATGCATGTAGTATGA
1021 ---------+---------+---------+---------+---------+---------+ 1080
       AAATTCAATTGAAGACCAGGTTCGACCATCATATTAAAGTATAGGTACGTACATCATACT AAACAGGATTGTGGTTATGAGTTCTCAAGAAAGCCTCTTTTCTGCACCCAGAGGCGAGG
1081 ---------+---------+---------+---------+---------+---------+ 1140
       TTTGTCCTAACACCAATACTCAAGAGTTCTTTCGGAGAAAAGACGTGGGTCTCCGCTCC

CAAGGAA
1141 ------- 1147
       GTTCCTT
```

FIG. 1C

```
      TGCTGCAGGCACATGGGGGTCATCTCTGGCTGGCAGGAAGGTGAGGGAGTCCTCTCTTCT
  1   ---------+---------+---------+---------+---------+---------+  60
      ACGACGTCCGTGTACCCCCAGTAGAGACCGACCGTCCTTCCACTCCCTCAGGAGAGAAGA

CTGGTCCTGGCTGACTCTGCCTCAGCAGGACTTCACTTGACCATTCTCACCTTCTGTCAC
  61  ---------+---------+---------+---------+---------+---------+ 120
      GACCAGGACCGACTGAGACGGAGTCGTCCTGAAGTGAACTGGTAAGAGTGGAAGACAGTG
                                                                      Intron 3
      CTCATCCTTAAAGTGACAGAGTAAATTAACTCTAAGGCCCCATCCAGGACTCAAGCTGTG
 121  ---------+---------+---------+---------+---------+---------+ 180
      GAGTAGGAATTTCACTGTCTCATTTAATTGAGATTCCGGGGTAGGTCCTGAGTTCGACAC TGATTTTACAAAAATGAAAATTATATTAATAATCCCATTGTAAAATCCCAAAAGAAAGTC
 181  ---------+---------+---------+---------+---------+---------+ 240
      ACTAAAATGTTTTTACTTTTAATATAATTATTAGGGTAACATTTTAGGGTTTTCTTTCAG
                                                  I3(-80)  G→A
      AAGAGACTAGCAGAAAGACAGGTGGGTGATGGGATGTCCTGGACAGAGCCTGGATCATGA
 241  ---------+---------+---------+---------+----+----+---------+ 300
      TTCTCTGATCGTCTTTCTGTCCACCCACTACCCTACAGGACCTGTCTCGGACCTAGTACT GGTCCCCATGTAGTGCTTGTACTACGCAGATGTTTCCTCTTGAGCTATTTTAAAGGTGTG
 301  ---------+---------+---------+---------+---------+-----+---+ 360(282)
      CCAGGGGTACATCACGAACATGATGCGTCTACAAAGGAGAACTCGATAAAATTTCCACAC
                                                                      Exon 4
      GAAAAAGCCAAAGCAATGCCCTCTCCACGGATACTAAAGACTCACCTTTCCACTCAGCTG
 361  ---------+---------+---------+---------+--------++------+---+ 420 (342)
      CTTTTTCGGTTTCGTTACGGGAGAGGTGCCTATGATTTCTGAGTGGAAAGGTGAGTCGAC
                                                         |
                              FIG. 1D                   332     Exon 3B
                                                        C→T     Splices in here
```

FIG. 1D

```
     CTGCCACCGTCTTTCTGGGAAAACAACTGCAAGGTAAGATACCAACAGCTCCCTGTGACA
421  ---------+---------+---------+---+-----+---------+---------+ 480
     GACGGTGGCAGAAAGACCCTTTTGTTGACGTTCCATTCTATGGTTGTCGAGGGACACTGT
                                                      I4(68)    C→A
     GAAGGGAAAGTAAGCCAACCAAAGCGAGTCCTGCAGACCCCAACGCAGAGCATTCGTGAT
481  ---------+---------+---------+---------+-+-------+---------+ 540
     CTTCCCTTTCATTCGGTTGGTTTCGCTCAGGACGTCTGGGGTTGCGTCTCGTAAGCACTA
           I4(94)      T→C
     CACCTTTGCCTCTCCACTGTCTCTGATGCTTACCAGCAAAGAGAAAACATAAAGTTCTAC
541  -----+-+-+---------+---------+---------+---------+---------+ 600
     GTGGAAACGGAGAGGTGACAGAGACTACGAATGGTCGTTTCTCTTTTGTATTTCAAGATG
                                                               Intron 4
     ATTCAGCAGGACATTCACCTGAACAGTTTCAAATAGGACATGAAGGCAGGATCCAGATTG
601  ---------+---------+---------+---------+---------+---------+ 660
     TAAGTCGTCCTGTAAGTGGACTTGTCAAAGTTTATCCTGTACTTCCGTCCTAGGTCTAAC AATGTTTGGAGGGAACTAGAGACATGGGGAGGCAGTGAGTGCAGTAAGCGTAGCTGTGAA
661  ---------+---------+---------+---------+---------+---------+ 720
     TTACAAACCTCCCTTGATCTCTGTACCCCTCCGTCACTCACGTCATTCGCATCGACACTT ATGAAGGGGAGAAGATGGTGGTCCCAGGCTGCAGGCCATGGGGAGGTTTTCTAACAGACC
721  ---------+---------+----------+---------+---------+---------+ 780
     TACTTCCCCTCTTCTACCACCAGGGTCCGACGTCCGGTACCCCTCCAAAAGATTGTCTGG

AGGGAGGGAAGAATGAGAG
781  ---------+---------
     TCCCTCCCTTCTTACTCTC
```

FIG. 1D-1

```
                              I4(-20)    C→T
     AAGTCCACTTTTTATACCATCTTTTACCCACCTCTTTTCTTACCCCAAAGTTCCTTTATG
301  ---------+---------+---------+---------+---------+---------+ 360 (385)
     TTCAGGTGAAAAATATGGTAGAAAATGGGTGGAGAAAAGAATGGGGTTTCAAGGAAATAC
                                                                   Exon 5

TAGCTCGAAATGCCAAAGACTGTATGGTTTCCTACTACCATTTCCAAAGGATGAACCACA
361  ---------+---------+---------+---------+---------+---------+ 420
     ATCGAGCTTTACGGTTTCTGACATACCAAAGGATGATGGTAAAGGTTTCCTACTTGGTGT

TGCTTCCTGACCCTGGTACCTGGGAAGAGTATTTTGAAACCTTCATCAATGGAAAAGTA
421  ---------+---------+---------+---------+---------+-------+-+ 480
     ACGAAGGACTGGGACCATGGACCCTTCTCATAAAACTTTGGAAGTAGTTACCTTTTCCAT

CGGGAACATCCTTCACACCCTTGCATTCTCACTCCAGCTAGGCTGGGTCTAGGGAACCAC
481  ---------+---------+---------+---------+---------+---------+ 540
     GCCCTTGTAGGAAGTGTGGGAACGTAAGAGTGAGGTCGATCCGACCCAGATCCCTTGGTG
                                       I5(97)    T→A
     AGGCAGCATTTTATCCCCTAGAATGCCTGTACTTCATCAGGTGTGTCCTACCACAGACTG
541  ---------+---------+---------+--+------+---------+---------+ 600
     TCCGTCGTAAAATAGGGGATCTTACGGACATGAAGTAGTCCACACAGGATGGTGTCTGAC

GGACTGGGCAGAGCAAGCTGGCCACTGAGTGTATGCCCACAGCCCTCAGCAAACATCTTC
601  ---------+---------+---------+---------+---------+---------+ 660
     CCTGACCCGTCTCGTTCGACCGGTGACTCACATACGGGTGTCGGGAGTCGTTTGTAGAAG
                                                                   Intron 5
     CACCTGATTCAGAGTCTTTAATTACAGCCATCCTCTTCCAAAAGGTGTCCTTGTCCCTAT
661  ---------+---------+---------+---------+---------+---------+ 720
     GTGGACTAAGTCTCAGAAATTAATGTCGGTAGGAGAAGGTTTTCCACAGGAACAGGGATA GTGATTGCACATAATAGGAAGCCACTTTAGGGACGATGTTGGGGCAAGTAACCCTAAGGC
721  ---------+---------+---------+---------+---------+---------+ 780
     CACTAACGTGTATTATCCTTCGGTGAAATCCCTGCTACAACCCCGTTCATTGGGATTCCG TGTCCCCATCTACACCACCCTCAAAATCAAACAGATCAGAACCCTTAGGACATATCTAAT
781  ---------+---------+---------+---------+---------+---------+ 840
     ACAGGGGTAGATGTGGTGGGAGTTTTAGTTTGTCTAGTCTTGGGAATCCTGTATAGATTA ACAGAATTTGGGTTTTCTCTCTAACTCACTTCAGGAAAATCCCTAATACTCAGAAGGT
841  ---------+---------+---------+---------+---------+---------+ 900
     TGTCTTAAACCCAAAAGAGAGAGATTGAGTGAAGTCCTTTTAGGGATTATGAGTCTTCCA TTTGTGTGATGCCTATGTAGACTATTCTGTTTCCTGTGTCTATTTCAGTGGTTTGGGGTT
901  ---------+---------+---------+---------+-------+-+---------+ 960 (514)
     AAACACACTACGGATACATCTGATAAGACAAAGGACACAGATAAAGTCACCAAACCCCAA
                                                                   Exon 6
     CCTGGTTTGACCACGTGAAAGGATGGTGGGAGATGAAAGACAGACACCAGATTCTCTTCC
961  ---------+---------+---------+---------+---------+---------+ 1020 (574)
     GGACCAAACTGGTGCACTTTCCTACCACCCTCTACTTTCTGTCTGTGGTCTAAGAGAAGG
```

FIG. 1E

```
                577   T→C
       TCTTCTATGAGGACATAAAGAGGGTGAGTGAAGGCTCTGCAGAAGAACCATTTTAAAGTG
1021   ------+---------+---+-----+---------+---------+---------+ 1080
       AGAAGATACTCCTGTATTTCTCCCACTCACTTCCGAGACGTCTTCTTGGTAAAATTTCAC
                                                  I6(73)   A→G                Intron 6
       GTTCTTCAGGTGCAGAGAAATTCAAAGTTGTTTCAAGGACATCCCAGAGAATTGTAGTA
1081   ---------+---------+---------+----+-+---+---------+---------+ 1140
       CAAGAAGTCCACGTCTCTTTAAGTTTCAACAAAGTTCCTGTAGGGTCTCTTAACATCAT TTTCTTTATGATACTCTCATTCATTCCAGTCCAATGTTACCCTTGCCGCAGGACCCAAAG
1141   ---------+---------+---------+---------+---------+---------+ 1200(606)
       AAAGAAATACTATGAGAGTAAGTAAGGTCAGGTTACAATGGGAACGGCGTCCTGGGTTTC
                                                         599
                                                         A→T
       CATGAAATTCGGAAGGTGATGCAGTTCATGGGAAAGAAGGTGGATGAAACAGTGCTAGAT
1201   ---------+---------+---------+---------+---------+---------+ 1260(666)
       GTACTTTAAGCCTTCCACTACGTCAAGTACCCTTTCTTCCACCTACTTTGTCACGATCTA     Exon 7
                                                    715  A→G
       AAAATTGTCCAGGAGACGTCATTTGAGAAAATGAAAGAAAATCCCATCACAAATCGTTCT
1261   ---------+---------+---------+---------+---------+---------+ 1320(726)
       TTTTAACAGGTCCTCTGCAGTAAACTCTTTTACTTTCTTTTAGGGTAGTGTTTAGCAAGA
                                763  T→G
       ACAGTTTCCAAATCTATCTTGGACCAGTCAATTTCCTCCTTCATGAGAAAAGGTGTGTGG
1321   ---------+---------+---------+---------+---------+---------+ 1380
       TGTCAAAGGTTTAGATAGAACCTGGTCAGTTAAAGGAGGAAGTACTCTTTTCCACACACC GGCCTCTTTATCATACATTCAGATTGTCTCGTAACATCCTGTCTGCCTCTTAGCAGACAA
1381   ---------+---------+---------+---------+---------+---------+ 1440
       CCGGAGAAATAGTATGTAAGTCTAACAGAGCATTGTAGGACAGACGGAGAATCGTCTGTT TATTGAGTTTTATTAATTCCAAGCCAATGCATTTCAACTATTCCTAATATGTGTTTCTAA
1441   ---------+---------+---------+---------+---------+---------+ 1500
       ATAACTCAAAATAATTAAGGTTCGGTTACGTAAAGTTGATAAGGATTATACACAAAGATT       Intron 7

TAAAACCAGGGATTTGATCCTGTTGTAGAAGAGAGCTTTCTAGGGTATTGTTCCAGTATT
1501   ---------+---------+---------+---------+---------+---------+ 1560
       ATTTTGGTCCCTAAACTAGGACAACATCTTCTCTCGAAAGATCCCATAACAAGGTCATAA

TGGTTGCAAGGAACAGAGAGTCCCTCAAGCTAGCCCCAAAGAAA
1561   ---------+---------+---------+---------+---- 1604
       ACCAACGTTCCTTGTCTCTCAGGGAGTTCGATCGGGGTTTCTTT
```

FIG. 1E-1

```
    TTGCTCAACATAATGTTTTGAGATTCCTCCATGTGGTTGTGTGTCTGTAGTTCATCATTC
1   ------------+---------+---------+---------+---------+---------+ 60
    AACGAGTTGTATTACAAAACTCTAAGGAGGTACACCAACACACAGACATCAAGTAGTAAG

TTTTATGTCTATGTAGTAATCCATCAGGTAAATACACTACAGGTGGGGCCAGGTCATGCA
61  ---------+---------+---------+---------+---------+---------+ 120
    AAAATACAGATACATCATTAGGTAGTCCATTTATGTGATGTCCACCCCGGTCCAGTACGT

GGCCACTAGCTGCCTTGGGTCAGTTGTCCAGCTGACTTAGAAGTCCATCCCCCTGCACAG
121 ---------+---------+---------+---------+---------+---------+ 180
    CCGGTGATCGACGGAACCCAGTCAACAGGTCGACTGAATCTTCAGGTAGGGGACGTGTC
                                                                  Intron 7
    AGTCCCCTAGGCCTGCTTCTTATAGGAGAGCTGCTCATGGACAGGTGTCCACTGAAGGGG
181 ---------+---------+---------+---------+---------+---------+ 240
    TCAGGGGATCCGGACGAAGAATATCCTCTCGACGAGTACCTGTCCACAGGTGACTTCCCC
                          ↓ I7(-101)     A insertion
    GAGTTGGGTGAGTCAGGTAT GTGGACAGGCCAGATTCAGTATGGGCACTACACCACTTTA
241 ---------+---------+---------+---------+---------+---------+ 300
    CTCAACCCACTCAGTCCATA CACCTGTCCGGTCTAAGTCATACCCGTGATGTGGTGAAAT
                        ↑
    CTCAGGGACACCACATCTTTCAATCAGAGTGACACTCCTGTCTGGCCTTCCTTTTTCTAG
301 ---------+---------+---------+---------+---------+---------+ 360
    GAGTCCCTGTGGTGTAGAAAGTTAGTCTCACTGTGAGGACAGACCGGAAGGAAAAAGATC
```

FIG. 1F

```
                GAACTGTGGGGGATTGGAAAAACCACTTCACTGTTGCCCAGAATGAGAGGTTTGATGAAA
(779) 361       ------------+---------+---------+---------+---------+---------+   420 (838)
                CTTGACACCCCCTAACCTTTTTGGTGAAGTGACAACGGGTCTTACTCTCCAAACTACTTT

TCTATAGAAGAAAGATGGAAGGAACCTCCATAAACTTCTGCATGGAACTCTGAGCAAGAT
      421       ------------+---------+---------+---------+---------+---------+   480 (898)
                AGATATCTTCTTTCTACCTTCCTTGGAGGTATTTGAAGACGTACCTTGAGACTCGTTCTA

GTAAATAAAATTAAAAGGTGGATGGCAAGAGTGCAAATACTATCTTCAATCCTTCAGTCC
      481       ------------+---------+---------+---------+---------+---------+   540 (958)
                CATTTATTTTAATTTTCCACCTACCGTTCTCACGTTTATGATAGAAGTTAGGAAGTCAGG
                                                                                   Exon 8

CAGCCAGAAGAATCTCTGAAAGCATATTGTGAATGTATACAATGTAGTACAAACAATCTC
      541       ------------+---------+---------+---------+---------+---------+   600 (1018)
                GTCGGTCTTCTTAGAGACTTTCGTATAACACTTACATATGTTACATCATGTTTGTTAGAG

TGTGATGATTAACAGTATGTCACCACTTCATTTTTAAAAAGGATCACGTCTAATGCCCA
      601       ------------+---------+---------+---------+---------+---------+   660 (1078)
                ACACTACTAATTGTCATACAGTGGTGAAGTAAAAAATTTTTCCTAGTGCAGATTACGGGT
                         1027 T→C

TTTTCCCAACTATTCTTTCCAAAGTAAGATATAAGGTAGCTTAATAAACTAAGTAAAACG
      661       ------------+---------+---------+---------+---------+---------+   720 (1138)
                AAAAGGGTTGATAAGAAAGGTTTCATTCTATATTCCATCGAATTATTTGATTCATTTTGC

TATGACTTGAGTACAAAAGGATTGTTTTAATCCCCATTATTCTGGAAAGTGCATCCTAGT
      721       ------------+---------+---------+---------+---------+---------+   780 (1198)
                ATACTGAACTCATGTTTTCCTAACAAAATTAGGGGTAATAAGACCTTTCACGTAGGATCA
                                                                        1191 A→G

CTCCCAGTCTATAACATCATAATACCTTGAGTATAAGTCCAAATATTAGGTTATATCTAT
      781       ------------+---------+---------+---------+---------+---------+   840 (1258)
                GAGGGTCAGATATTGTAGTATTATGGAACTCATATTCAGGTTTATAATCCAATATAGATA
                 1260 T→C           1217 A→G                        1251 A→G

ATTAAAAACAAAATTTCTGTCATCTGTCCTGGCCATTCAGGCAACTCCAGCCTGGGCTCA
      841       ------------+---------+---------+---------+---------+---------+   900 (1318)
                TAATTTTTGTTTTAAAGACAGTAGACAGGACCGGTAAGTCCGTTGAGGTCGGACCCGAGT
                                                                                   3' Flanking ATCCTGGAGTTCTGTCTGGTCACTATCAGAAGGAACACTTTGAGGGAAACCCTGGTGCAG
      901       ------------+---------+---------+---------+---------+---------+   960 (1378)
                TAGGACCTCAAGACAGACCAGTGATAGTCTTCCTTGTGAAACTCCCTTTGGGACCACGTC CCAGCCCTGAGGAAACATGGCCTGAGTGCCCTCACTGGTGGGTGGGAATAAAATGGAAGT
      961       ------------+---------+---------+---------+---------+---------+   1020 (1438)
                GGTCGGGACTCCTTTGTACCGGACTCACGGGAGTGACCACCCACCCTTATTTTACCTTCA GCACAGAGGAGATGTCAGAAGACCAAAACTTGGTGAATAGTCCCAGTGCTAGGTCATATA
     1021       ------------+---------+---------+---------+---------+---------+   1080 (1498)
                CGTGTCTCCTCTACAGTCTTCTGGTTTTGAACCACTTATCAGGGTCACGATCCAGTATAT
```

```
atggccctga cctcagacct ggggaaacag ataaaactga aagaggtgga gggacccctc
ctgcagcctg caactgtgga caactggagc cagatccaga gcttcgaggc caaaccagat
gatcctctca tctgcaccta ccctaaagca gggacaacgt ggattcagga aattgtggat
atgattgaac agaatgggga cgtggagaag tgccagcgag ccatcatcca acaccgccat
cctttcattg agtgggctcg gccaccccaa ccttctggtg tgaaaaaagc caaagcaatg
ccctctccac ggatactaaa gactcacctt tccactcagc tgctgccacc gtctttctgg
gaaaacaact gcaagttcct ttatgtagct aagactgtat ggtttcctac
taccatttcc aaaggatgaa ccacatgctt cctgacccty gtacctggga agagtatttt
gaaaccttca tcaatggaaa agtggtttgg ccagattctc ttcctcttct atgaggacat
tgggagatga aagacagaca ccagatcgga ggtgatgcag agaaggtgga aaagaggga
ccaagcatg aaattccagga gacgtcattt ttcatggaaa cagtcaatga aagaaaatcc catgacaaat
ctagataaaa ttgtccagga gactcattt gagaaaatga ctcccttcat gagaaaaagga
cgttctacag tttccaaatc tatccttgac cagtcaattt gtgcccaga atgagaggtt tgatgaaatc
actgtggggg attggaaaaa ccacttcact gttgcccaga atgagaggtt tgatgaaatc
tatagaagaa agatggaagg aacctccata aacttctgca tggaactctg a (SEQ ID NO:26)
```

Figure 2B

MALTSDLGKQIKLKEVEGTLLQPATVDNWSQIQSFEAKPDDLLICTYPKAGTTWIQEIVDMIEQNGD
VEKCQRAIIQHRHPFIEWARPPQPSGVEKAKAMPSPRILKTHLSTQLLPPSFWENNCKFLYVARNA
KDCMVSYYHFQRMNHMLPDPGTWEEYFETFINGKVVWGSWFDHVKGWWEMKDRHQILFLFYE
DIKRDPKHEIRKVMQFMGKKVDETVLDKIVQETSFEKMKENPMTNRSTVSKSILDQSISSFMRKGT
VGDWKNHFTVAQNER FDEIYRRKMEGTSINFCMEL (SEQ ID NO:2)

SULFOTRANSFERASE SEQUENCE VARIANTS

CROSS-REFERENCE TO RELATED APPLICATIONS

This application is a continuation of U.S. Ser. No. 09/792,695, filed Feb. 23, 2001, now U.S. Pat. No. 7,026,163.

STATEMENT AS TO FEDERALLY SPONSORED RESEARCH

Funding for the work described herein was provided in part by grant nos. GM28157, GM35720, and GM61388, awarded by the National Institutes of Health. The federal government has certain rights in the invention.

TECHNICAL FIELD

The invention relates to sulfotransferase nucleic acid and amino acid sequence variants.

BACKGROUND

Sulfate conjugation is an important pathway in the biotransformation of many neurotransmitters, hormones, drugs and other xenobiotics, and is catalyzed by cytosolic sulfotransferase enzymes designated "SULT." SULT enzymes are encoded by a gene superfamily, which, in mammals, is divided into two families, SULT1 or phenol SULTs and SULT2 or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) subfamilies. SULT2 subfamilies include two hydroxysteroid SULTs, 2A1 and 2B1.

Members of the SULT1C subfamily, including SULT1C1 and SULT1C2, catalyze the sulfate conjugation of thyroid hormones and carcinogenic hydroxyarylamines. A human SULT1C1 cDNA, which was cloned from a fetal liver-spleen cDNA library, encodes a protein that is 62% identical to the amino acid sequence of a rat SULT designated "ST1C1". Her et al., *Genomics* (1997) 41: 467-470. ST1C1 catalyzes the metabolic activation of the procarcinogen N-hydroxy-2-acetylaminofluorene. The amino acid sequences of human SULT1C1 and human SULT1C2 are 62.6% identical. Sakakibara et al., *J. Biol. Chem.* (1998) 273:33929-33935. Human SULT1C1 is highly expressed in stomach, kidney, liver, and thyroid, while SULT1C2 is highly expressed in fetal lung and fetal kidney.

SUMMARY

The invention is based on the discovery of sequence variants that occur in both coding and non-coding regions of SULT1C1 nucleic acids. Certain SULT1C1 nucleotide sequence variants encode SULT1C1 enzymes that are associated with individual differences in enzymatic activity. Other SULT1C1 sequence variants in non-coding regions of the SULT1C1 nucleic acid may alter regulation of transcription and/or splicing of the SULT1C1 nucleic acid. Discovery of these sequence variants allows individual differences in the sulfate conjugation of drugs and other xenobiotics in humans to be assessed such that particular treatment regimens can be tailored to an individual based on the presence or absence of one or more sequence variants. Identification of SULT1C1 sequence variants also allows predisposition to hormone dependent diseases or chemical carcinogenesis to be assessed in individuals.

In one aspect, the invention features an isolated nucleic acid molecule that includes a SULT1C1 nucleic acid sequence, wherein the nucleic acid molecule is at least ten nucleotides in length, and wherein the SULT1C1 nucleic acid sequence includes a nucleotide sequence variant. The nucleotide sequence variant can be within a coding sequence, an intron sequence, a 5' untranslated sequence, or a 3' untranslated sequence, and can be a nucleotide deletion, a nucleotide insertion, or a nucleotide substitution. The nucleotide sequence variant can be at one or more positions selected from the group consisting of 179, 218, 332, 577, 599, 715, and 763 relative to the adenine of the SULT1C1 translation initiation codon, e.g., at one or more positions selected from the group consisting of a cytosine substitution for adenine at position 179, an adenine substitution for guanine at position 218, a thymine substitution for cytosine at position 332, a cytosine substitution for thymine at position 577, a thymine substitution for adenine at position 599, a guanine substitution for adenine at position 715, and a guanine substitution for thymine at position 763.

The nucleotide sequence variant can be at position 37 relative to the guanine in the splice donor site of intron 1, e.g., a cytosine substitution for thymine. The nucleotide sequence variant can be at position 61 or 62 relative to the guanine in the splice donor site of intron 3, e.g., a variant selected from the group consisting of a cytosine deletion at position 61, a thymine deletion at position 62, and a cytosine and thymine deletion at positions 61 and 62, respectively. The nucleotide sequence variant can be at position 107 relative to the guanine in the splice donor site of intron 3. The nucleotide sequence variant can be a deletion comprising the nucleotide sequence of 5'-TCTCTCCTTCCTCTTTTCTCTCTCCCTCCC-3' (SEQ ID NO:3). The nucleotide sequence variant can be at one or more positions selected from the group consisting of −80, −2158, −2177, and −2377 relative to the guanine in the splice acceptor site of intron 3, e.g., at one or more positions selected from the group consisting of an adenine substitution for guanine at position −80, a thymine substitution for cytosine at position −2158, a thymine substitution for cytosine at position −2177, and a thymine insertion at position −2377.

The nucleotide sequence variant can be at position 68 or 94 relative to the guanine in the splice donor site of intron 4, e.g., selected from the group consisting of an adenine substitution for cytosine at position 68 and a cytosine insertion for thymine at position 94. The nucleotide sequence variant can be at position −20 relative to the guanine in the splice acceptor site of intron 4, e.g., a thymine substitution for cytosine. The nucleotide sequence variant can be at position 97 relative to the guanine in the splice donor site of intron 5, e.g., an adenine substitution for thymine. The nucleotide sequence variant can be at position 73 relative to the guanine in the splice donor site of intron 6, e.g., a guanine substitution for adenine. The nucleotide sequence variant can be at position −101 relative to the guanine in the splice acceptor site of intron 7, e.g., an adenine insertion. The nucleotide sequence variant can be at one or more positions selected from the group consisting of −149, −258, −500, −518, −547, and −760 relative to the adenine of the SULT1C1 translation initiation codon, e.g., at one or more positions selected from the group consisting of a cytosine insertion at position −149, a thymine substitution for cytosine at position −258, a cytosine substitution for thymine at position −500, a thymine substitution for cytosine at position −518, a guanine substitution for adenine at position −547, and a guanine substitution for thymine at position −760.

The nucleotide sequence variant can be at one or more positions selected from the group consisting of 1027, 1191, 1217, 1251, or 1260 relative to the adenine of the SULT1C1 translation initiation codon, e.g., at one or more positions selected from the group consisting of a cytosine substitution for thymine at position 1027, a guanine substitution for adenine at position 1191, a guanine substitution for adenine at position 1217, a guanine substitution for adenine at position 1251, and a cytosine substitution for thymine at position 1260.

The invention also features an isolated nucleic acid encoding a SULT1C1 polypeptide, wherein the polypeptide includes a SULT1C1 amino acid sequence variant. The amino acid sequence variant can be at one or more residues selected from the group consisting of 60, 73, 111, 193, 200, 239, and 255.

In another aspect, the invention features an isolated SULT1C1 polypeptide, wherein the polypeptide includes a SULT1C1 amino acid sequence variant. The polypeptide can include a SULT1C1 amino acid sequence variant at one or more residues selected from the group consisting of 60, 73, 111, 193, 200, 239, and 255. For example, the amino acid sequence variant at residue 60 can be an alanine; the amino acid sequence variant at residue 73 can be a glutamine; the amino acid sequence variant at residue 111 can be a phenylalanine; the amino acid sequence variant at residue 193 can be a leucine; the amino acid sequence variant at residue 200 can be a valine; the amino acid sequence variant at residue 239 can be an alanine; or the amino acid sequence variant at residue 255 can be an alanine. The amino acid sequence variant can be at residues 200 and 239, 60 and 255, or 73 and 255. Activity of the polypeptide can be altered relative to a wild type SULT1C1 polypeptide.

In yet another aspect, the invention features an article of manufacture that includes a substrate, wherein the substrate includes a population of isolated SULT1C1 nucleic acid molecules, each nucleic acid molecule including a SULT1C1 nucleotide sequence variant. The substrate can include a plurality of discrete regions, wherein each region includes a different population of isolated SULT1C1 nucleic acid molecules, and wherein each population of molecules includes a different SULT1C1 nucleotide sequence variant.

The invention also features a method for determining if a mammal is predisposed to a thyroid disease. The method includes providing a biological sample from the mammal, and detecting the presence or absence of a SULT1C1 nucleotide sequence variant in the sample, wherein predisposition to a thyroid disease is determined based on the presence or absence of the variant. The method further can include detecting the presence or absence of a plurality of the SULT1C1 nucleotide sequence variants in the sample to obtain a variant profile of the mammal, and wherein predisposition to a thyroid disease is determined based on the variant profile.

In another aspect, the invention features a method for determining if a mammal is predisposed to cancer. The method includes providing a biological sample from the mammal, and detecting the presence or absence of a SULT1C1 nucleotide sequence variant in the sample, wherein predisposition to cancer is determined based on the presence or absence of the variant. The method further can include detecting the presence or absence of a plurality of the SULT1C1 nucleotide sequence variants in the sample to obtain a variant profile of the mammal, and wherein predisposition to cancer is determined based on the variant profile. The cancer can be a chemically induced cancer.

The invention also features a method for obtaining a SULT1C1 variant profile. The method includes providing a biological sample from a mammal, and detecting the presence or absence of a plurality of SULT1C1 nucleotide sequence variants in the sample to obtain a variant profile of the mammal. The method further can include communicating the profile to a medical or research professional.

In another aspect, the invention features a method for determining the sulfonator status of a subject. The method includes determining whether the subject comprises a variant SULT1C1 nucleic acid. The variant SULT1C1 nucleic acid can contain a nucleotide sequence variant at a position selected from the group consisting of nucleotide 179 of SEQ ID NO:26, nucleotide 218 of SEQ ID NO:26, nucleotide 332 of SEQ ID NO:26, and nucleotide 763 of SEQ ID NO:26. The variant SULT1C1 nucleic acid can have an adenine at position 179 of SEQ ID NO:26, a cytosine at position 218 of SEQ ID NO:26, a guanine at position 332 of SEQ ID NO:26, or a guanine at position 763 of SEQ ID NO:26. The determining step can include a) providing a biological sample from the subject, and b) detecting the presence or absence of a SULT1C1 nucleotide sequence variant in the sample.

Other features and advantages of the invention will be apparent from the following detailed description, and from the claims.

DESCRIPTION OF DRAWINGS

FIGS. 1A-1F are the nucleotide sequence of the reference SULT1C1. Single nucleotide polymorphisms (SNPs) are circled, insertions are indicated with a line, and deletions are indicated by two lines that bound the deleted sequence. The position and nature of each SNP, insertion, and deletion is indicated proximal to the markings described. Exons are bounded by boxes to differentiate exon and intron sequences. Exon and intron numbers are also indicated in the margins. The start codon is indicated by a box within exon 2, and the stop codon, as well as two polyadenylation signal sequences, are indicated by boxes within exon 8. FIG. 1A (SEQ ID NO:1, top strand; SEQ ID NO:32, bottom strand) includes 5' flanking region, exon 1, and part of intron 1; FIG. 1B (SEQ ID NO:27, top strand; SEQ ID NO:33, bottom strand) includes part of intron 1, exon 2, intron 2, exon 3, and part of intron 3; FIG. 1C (SEQ ID NO:28, top strand; SEQ ID NO:34, bottom strand) includes part of intron 3, exon 3b, and part of intron 3; FIG. 1D (SEQ ID NO:29, top strand; SEQ ID NO:35, bottom strand) includes part of intron 3, exon 4, and part of intron 4. Positions 1-355 correspond to nucleotides −354 to −1 of intron 3. Positions 356-453 correspond to nucleotides 278 to 375 of the cDNA sequence. Positions 454-799 correspond to nucleotides 1 to 346. of intron 4; FIG. 1E (SEQ ID NO:30, top strand; SEQ ID NO:36, bottom strand) includes part of intron 4, exon 5, intron 5, exon 6, intron 6, exon 7, and part of intron 7; FIG. 1F (SEQ ID NO:31, top strand; SEQ ID NO:37, bottom strand) includes part of intron 7, exon 8, and a 3' flanking region. Positions 1-360 correspond to nucleotides −360 to −1 of intron 7. Positions 361-721 correspond to nucleotides 779 to 1139 of the cDNA sequence. Intron 3 is approximately 7.0 kilobases, intron 4 is approximately 3.8 kilobases, and intron 7 is approximately 3.0 kilobases.

FIGS. 2A (SEQ ID NO:26) and 2B (SEQ ID NO:2) are the cDNA and amino acid sequences of the reference SULT1C1, respectively.

DETAILED DESCRIPTION

Figure 3:
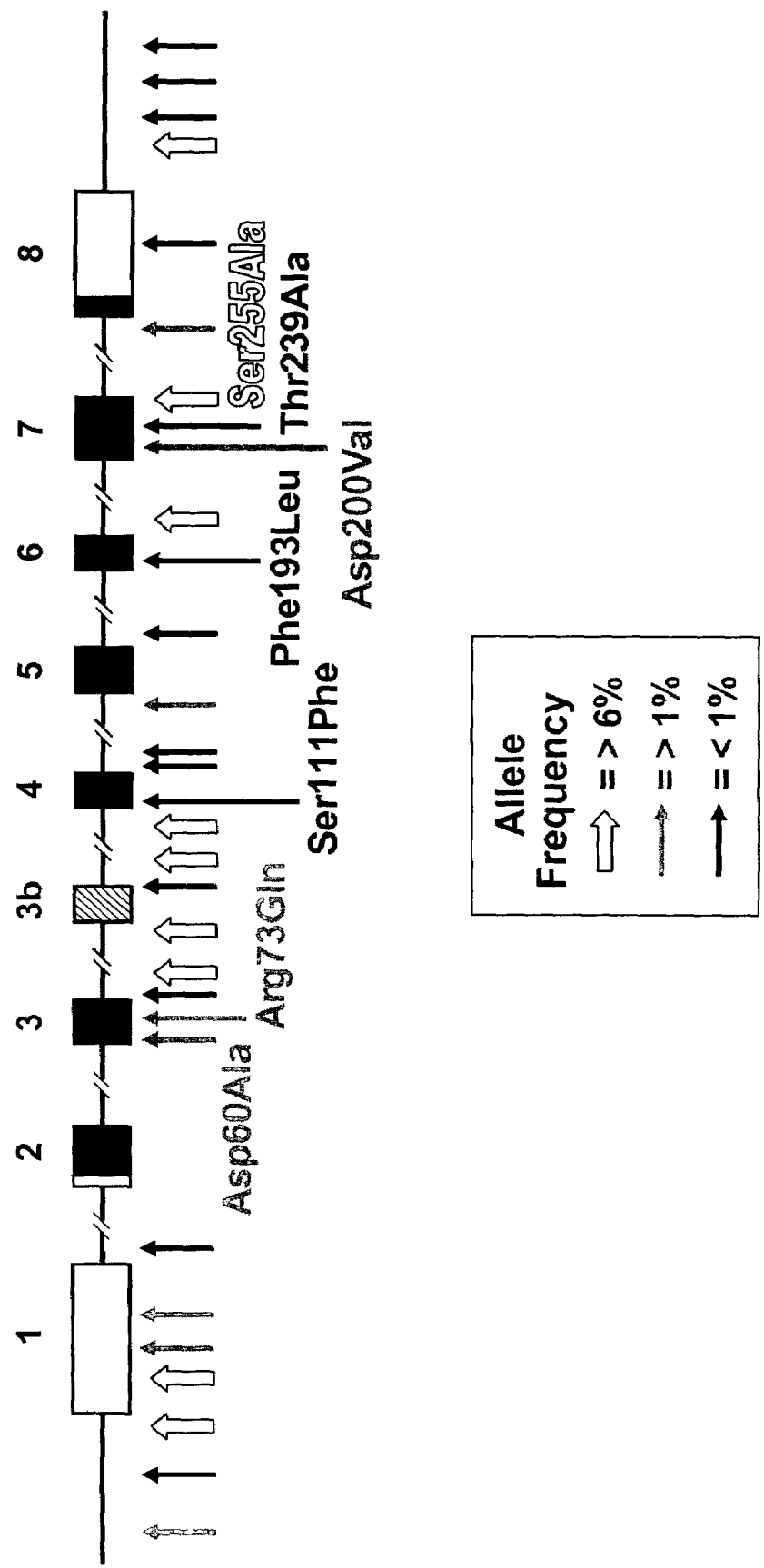
FIG. 3 is a schematic of the location of the non-synonymous polymorphisms within the SULT1C1 sequence.

The invention features SULT1C1 nucleotide and amino acid sequence variants. SULT1C1 catalyzes the transfer of inorganic sulfate to planar phenols, including hydroxyarylamines, and uses 3'-phosphoadenosine-5'-phosposulfate (PAPS) as the sulfate donor. Sulfation typically detoxifies compounds as the resulting ionized, organic sulfates are more readily excreted than the unsulfated compounds. Furthermore, functional groups that may interact with biological macromolecules such as nucleic acids or proteins can be masked by the sulfate moiety. For example, SULT1C1 may play a role in thyroid hormone inactivation. Thyroid hormone levels are determined primarily by sulfation, which increases the rate of deiodination and subsequent inactivation. Sulfation of certain compounds, however, such as the hydroxy metabolite of 2-acetylaminofluorene (AAF), produces sulfate conjugates that are chemically unstable and that can degrade to form reactive, electrophilic species. In particular, sulfation of the hydroxy metabolite of AAF produces a reactive N—O-sulfate ester, which can rearrange and fragment into a reactive electrophilic species that can bind to nucleic acids and proteins. Thus, detecting sulfotransferase nucleic acid and amino acid sequence variants facilitates the prediction of therapeutic efficacy and toxicity of drugs on an individual basis, as well as the ability to biotransform certain hormones and neurotransmitters.

Nucleic Acid Molecules

The invention features isolated nucleic acids that include a SULT1C1 nucleic acid sequence. The SULT1C1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-SULT1C1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids of the invention can be in sense or antisense orientation, can be complementary to the SULT1C1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in the SULT1C1 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference SULT1C1 nucleic acid sequence is provided in FIG. 1 (SEQ ID NOS:1, 27, 28, 29, 30, and 31) and in GenBank (Accession Nos. U66036, AF186251-AF186256, and AF186257-AF186262). The reference SULT1C1 amino acid sequence is provided in FIG. 2 (SEQ ID NO:2) and in GenBank (Accession No. U66036). The nucleic acid and amino acid reference sequences also are referred to herein as "wild type". As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences are designated as "−X" relative to the "A" in the initiation codon; positions of nucleotide sequence variants in the coding sequence and 3' untranslated sequence are designated as "+X" or "X" relative to the "A" in the initiation codon. Nucleotide sequence variants that occur in introns are designated as "+X" or "X" relative to "G" in the splice donor site (GT) or as "−X" relative to the "G" in the splice acceptor site (AG).

In some embodiments, a SULT1C1 nucleotide sequence variant encodes a SULT1C1 polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-300 residues, or a full-length SULT1C1 polypeptide). SULT1C1 polypeptides may or may not have sulfotransferase catalytic activity, or may have altered activity relative to the reference SULT1C1 polypeptide. Polypeptides that do not have activity or have altered activity are useful for diagnostic purposes (e.g., for producing antibodies having specific binding affinity for variant sulfotransferase polypeptides).

Corresponding SULT1C1 polypeptides, irrespective of length, that differ in amino acid sequence are herein referred to as allozymes. For example, a SULT1C1 nucleic acid sequence that includes a cytosine at nucleotide 179 encodes a SULT1C1 polypeptide having an alanine at amino acid residue 60. This polypeptide (Asp60Ala) would be considered an allozyme with respect to the reference SULT1C1 polypeptide that contains an aspartic acid at amino acid residue 60. Additional non-limiting examples of SULT1C1 sequence variants that alter amino acid sequence include variants at nucleotides 218, 332, 577, 599, 715, and 763. For example, a SULT1C1 nucleic acid molecule can include an adenine at nucleotide 218 and encode a SULT1C1 polypeptide having a glutamine at amino acid residue 73 in place of an arginine residue (Arg73Gln); a thymine at nucleotide 332 and encode a SULT1C1 polypeptide having a phenylalanine at amino acid 111 in place of a serine (Ser111Phe); a cytosine at nucleotide 577 and encode a SULT1C1 polypeptide having a leucine residue at amino acid 193 in place of a phenylalanine (Phe193Leu); a thymine at nucleotide 599 and encode a SULT1C1 polypeptide having a valine at amino acid 200 in place of an aspartic acid (Asp200Val); a guanine at nucleotide 715 and encode a SULT1C1 polypeptide having an alanine at amino acid 239 in place of a threonine (Thr239Ala); or a guanine at nucleotide 763 and encode a SULT1C1 polypeptide having an alanine at amino acid 255 in place of a serine (Ser255Ala). In addition, a SULT1C1 nucleic acid can encode an allozyme having two or more amino acid variants, e.g., the nucleic acid can have variations at nucleotides 599 and 715, 179 and 763, and 218 and 763.

SULT1C1 allozymes as described above are encoded by a series of sulfotransferase alleles. These alleles represent nucleic acid sequences containing sequence variants, typically multiple sequence variants, within coding and non-coding sequences. Representative examples of single nucleotide variants are described above. Table 2 sets out a series of SULT1C1 alleles that encode SULT1C1. Alleles encoding Arg73Gln, Asp200Val, and Ser255Ala are commonly observed, (allele frequencies >1%). The relatively large number of alleles and allozymes for SULT1C1 indicates the potential complexity of SULT pharmacogenetics. Such complexity emphasizes the need for determining single nucleotide variants, (i.e., single nucleotide polymorphisms, SNPs) as well as complete haplotypes (i.e., the set of alleles on one chromosome or a part of a chromosome) of patients.

Certain SULT1C1 nucleotide sequence variants do not alter the amino acid sequence. Such variants, however, could alter regulation of transcription as well as mRNA stability. SULT1C1 variants can occur in intron sequences, for example, within introns 1, 2, 3, 4, 5, 6, or 7. In particular, the nucleotide sequence variant can include a cytosine at nucleotide 37 of intron 1. Intron 3 variants can include a deletion of "CT" at 61-62, a deletion of a 30 bp sequence at 107 (5'-TCTCTCCTTCCTCTTTTCTCTCTCCCTCCC-3', SEQ ID NO:3), insertion of a thymine at −2377, substitution of a thymine at −2177, substitution of a thymine at −2158, or substitution of an adenine at −80. Intron 4 variants include substitution of an adenine at 68, a cytosine at 94, or a thymine at −20. Intron 5 sequence variants can include substitution of an adenine at 97. Intron 6 sequence variants can include a substitution of a guanine at 73. Intron 7 variants can include an insertion of an adenine at −101.

SULT1C1 nucleotide sequence variants that do not change the amino acid sequence also can be within an exon or in 5' or 3' untranslated sequences. For example, the 5' flanking region of SULT1C1 can include a substitution of a guanine at −760, a guanine at −547, a thymine at −518, or a cytosine at −500 and the 5' UTR can include a substitution of a thymine at −258 or an insertion of a cytosine at −149. The 3' UTR can contain a cytosine at 1027 and the 3' flanking region can include a guanine at 1191, a guanine at 1217, a guanine at 1251, and a cytosine at 1260.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a SULT1C1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis *Genetic Engineering News,* 12(9):1 (1992); Guatelli et al., *Proc. Natl. Acad. Sci. USA,* 87:1874-1878 (1990); and Weiss, *Science,* 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIG. 1 can be mutated using standard techniques including oligonucleotide-directed mutagenesis and site-directed mutagenesis through PCR. See, *Short Protocols in Molecular Biology,* Chapter 8, Green Publishing Associates and John Wiley & Sons, Edited by Ausubel, F. M et al., 1992. Examples of positions that can be modified are described above.

SULT1C1 Polypeptides

Isolated SULT1C1 polypeptides of the invention include an amino acid sequence variant relative to the reference SULT1C1 (FIG. 2B, GenBank Accession No. U66036). The term "isolated" with respect to a SULT1C1 polypeptide refers to a polypeptide that has been separated from cellular components that naturally accompany it. Typically, the polypeptide is isolated when it is at least 60% (e.g., 70%, 80%, 90%, 95%, or 99%), by weight, free from proteins and naturally-occurring organic molecules that are naturally associated with it. In general, an isolated polypeptide will yield a single major band on a non-reducing polyacrylamide gel.

SULT1C1 polypeptides of the invention include variants at one or more of residues 60, 73, 111, 193, 200, 239, and 255. In particular, an alanine residue can be substituted at position 60, a glutamine residue at position 73, a phenylalanine at position 111, a leucine at position 193, a valine at position 200, an alanine at position 239, or an alanine at position 255. SULT1C1 polypeptides may have more than one amino acid substitution. For example, a SULT1C1 polypeptide can have a valine at amino acid 200 and an alanine at amino acid 239, an alanine at amino acid 60 and an alanine at amino acid 255, or a glutamine at amino acid 73 and an alanine at amino acid 255.

In some embodiments, activity of SULT1C1 polypeptides is altered relative to the reference SULT1C1. As described herein, certain SULT1C1 allozymes have reduced activity (e.g., Asp60Ala, Arg73Gln, Ser111Phe, Phe193Leu, Asp200Val, Thr239Ala, and Asp200Val,Thr239Ala), while other allozymes (Ser255Ala) have activity that is comparable to the reference SULT1C1. Other allozymes can have increased activity relative to the reference SULT1C1. Activity of SULT1C1 polypeptides can be assessed in vitro using a sulfate acceptor substrate such as 4-nitrophenol (4-NP, Sigma Chemical Co., St. Louis, Mo.) and a donor sulfate molecule such as PAPS. In general, recombinant SULT1C1 polypeptides can be incubated at 37° C. with 10 mM of sulfate acceptor substrate in a potassium phosphate buffer (5 mM, pH 7.4) and 0.4 µM labeled PAPS (e.g., $^{35}$S-PAPS from New England Nuclear Life Science Products, Inc., Boston Mass.). Reactions can be stopped by precipitating PAPS and SULT1C1 polypeptide (e.g., with barium hydroxide, barium acetate, and zinc sulfate). After centrifugation of the reaction, radioactivity in the supernatant is assessed. SULT1C1 activity is expressed as nmoles of sulfate conjugated product formed per hour of incubation. See, Campbell, N. R. C. et al., *Biochem. Pharmacol.*, 36:1435-1446 (1987).

Other biochemical properties of allozymes, such as apparent Km values, also can be altered relative to the reference SULT1C1. Apparent Km values can be calculated, for example, by using the method of Wilkinson with a computer program written by Cleland. Wilkinson, *Biochem. J.*, 80:324-332 (1961); and Cleland, *Nature*, 198:463-365 (1963). As described herein, the apparent Km values for PAPS vary 7-fold among the allozymes tested (Asp60Ala, Arg73Gln, Phe193Leu, Asp200Val, Thr239Ala, and Ser255Ala).

Isolated polypeptides of the invention can be obtained, for example, by extraction from a natural source (e.g., liver tissue), chemical synthesis, or by recombinant production in a host cell. To recombinantly produce SULT1C1 polypeptides, a nucleic acid sequence encoding a sulfotransferase variant polypeptide can be ligated into an expression vector and used to transform a bacterial or eukaryotic host cell (e.g., insect, yeast, or mammalian cells). In general, nucleic acid constructs include a regulatory sequence operably linked to a sulfotransferase nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express sulfotransferase variant polypeptides. A nucleic acid encoding a polypeptide of the invention can be cloned into, for example, a baculoviral vector such as pBlueBac (Invitrogen, San Diego, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Mammalian cell lines that stably express sulfotransferase variant polypeptides can be produced by using expression vectors with the appropriate control elements and a selectable marker. For example, the eukaryotic expression vector pCR3.1 (Invitrogen, San Diego, Calif.) and p91023(B) are suitable for expression of sulfotransferase variant polypeptides in, for example, Chinese hamster ovary (CHO) cells, COS-1 cells, human embryonic kidney 293 cells, NiH3T3 cells, BHK21 cells, MDCK cells, and human vascular endothelial cells (HUVEC). Following introduction of the expression vector by electroporation, liptofectin, calcium phosphate or calcium chloride co-precipitation, DEAE dextran, or other suitable method, stable cell lines are selected, e.g., by antibiotic resistance to G418, kanamycin, or hygromycin. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

SULT1C1 variant polypeptides can be purified by known chromatographic methods including DEAE ion exchange, gel filtration, and hydroxylapatite chromatography. Van Loon and Weinshilboum, *Drug Metab. Dispos.*, 18:632-638 (1990); Van Loon et al., *Biochem. Pharmacol.*, 44:775-785 (1992). SULT1C1 polypeptides can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase. Immunoaffinity chromatography also can be used to purify SULT1C1 polypeptides.

Non-Human Mammals

The invention features non-human mammals that include SULT1C1 nucleic acids of the invention, as well as progeny and cells of such non-human mammals. Non-human mammals include, for example, rodents such as rats, guinea pigs, and mice, and farm animals such as pigs, sheep, goats, horses and cattle. Non-human mammals of the invention can express a SULT1C1 variant nucleic acid in addition to an endogenous SULT1C1 (e.g., a transgenic non-human that includes a SULT1C1 nucleic acid randomly integrated into the genome of the non-human mammal). Alternatively, an endogenous SULT1C1 nucleic acid can be replaced by a SULT1C1 variant nucleic acid of the invention through homologous recombination. See, Shastry, B. S., *Mol. Cell Biochem.*, (1998) 181 (1-2):163-179, for a review of gene targeting technology.

In one embodiment, non-human mammals are produced that lack an endogenous SULT1C1 nucleic acid (i.e., a knockout), then a SULT1C1 variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent". Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous SULT1C1 nucleic acid. That is, cultured ES cells can be transformed with a knockout construct and cells selected in which the SULT1C1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., "Molecular Cloning, A Laboratory Manual, second edition, Cold Spring Harbor Press, Plainview; N.Y., 1989.

To generate a knockout animal, ES cells having at least one inactivated SULT1C1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated SULT1C1 allele. If the original ES cell was heterozygous for the inactivated SULT1C1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are "totipotent", i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the SULT1C1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated SULT1C1 gene, and then fused with enucleated oocytes. After activation of the oocytes, the eggs are cultured to the blastocyst stage, and implanted into a recipient. See, Cibelli, J. B. et al., *Science,* (1998) 280:1256-1258. Adult somatic cells, including, for example, cumulus cells and mammary cells, can be used to produce animals such as mice and sheep, respectively. See, for example, Wakayama, T. et al., *Nature,* (1998) 394(6691):369-374; and Wilmut, I. et al., *Nature,* (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama, T. et al., 1998, supra.

Non-human mammals of the invention such as mice can be used to screen, for example, toxicity of compounds that are substrates for SULT1C1, drugs that alter SULT1C1 activity, or for carcinogenesis. For example, SULT1C1 activity or toxicity can be assessed in a first group of such non-human mammals in the presence of a compound, and compared with SULT1C1 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally and parenterally. For example, the compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols.

Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Detecting Sulfotransferase Sequence Variants

Sulfotransferase nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33-39), denaturing high performance liquid chromatography (DHPLC, Underhill et al., 1997, *Genome Res.,* 7:996-1005), infared matrix-assisted laser desorption/ionization (IR-MALDI) mass spectrometry (WO 99/57318), and combinations of such methods.

Genomic DNA generally is used in the analysis of sulfotransferase nucleotide sequence variants. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.) and the A.S.A.P.™ Genomic DNA isolation kit (Boehringer Mannheim, Indianapolis, Ind.).

Typically, an amplification step is performed before proceeding with the detection method. For example, exons or introns of the sulfotransferase gene can be amplified then directly sequenced. Dye primer sequencing can be used to increase the accuracy of detecting heterozygous samples.

Allele specific hybridization also can be used to detect sequence variants, including complete haplotypes of a mammal. See, Stoneking et al., 1991, *Am. J. Hum. Genet.* 48:370-382; and Prince et al., 2001, *Genome Res.,* 11(1):152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For SULT1C1 sequence variants that do not alter a common restriction site, mutagenic primers can be designed that introduce a restriction site when the variant allele is present or when the wild type allele is present. A portion of SULT1C1 nucleic acid can be amplified using the mutagenic primer and a wild type primer, followed by digest with the appropriate restriction endonuclease.

Certain variants, such as insertions or deletions of one or more nucleotides (e.g., deletion of a 30 bp sequence in intron 3), change the size of the DNA fragment encompassing the variant. The insertion or deletion of nucleotides can be assessed by amplifying the region encompassing the variant and determining the size of the amplified products in comparison with size standards. For example, the intron 3 region of SULT1C1 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1): 163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, sulfotransferase variants can be detected by antibodies that have specific binding affinity for variant sulfotransferase polypeptides. Variant sulfotransferase polypeptides can be produced in various ways, including recombinantly, as discussed above. Host animals such as rabbits, chickens, mice, guinea pigs and rats can be immunized by injection of a sulfotransferase variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a sulfotransferase variant polypeptide and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77-96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a sulfotransferase variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246: 1275 (1989). Once produced, antibodies or fragments thereof are tested for recognition of sulfotransferase variant polypeptides by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992.

Methods of the Invention

As a result of the present invention, it is now possible to determine sulfonator status of a mammal (e.g., a human subject) as well as to determine if a mammal is predisposed to thyroid disease or cancer. "Sulfonator status" refers to the ability of a mammal to transfer a sulfate group to a substrate (e.g., thyroid hormone). Predisposition refers to a relative greater risk for development of a disease such as hypothyroidism or hyperthyroidism, or a chemically induced cancer. Presence of SULT1C1 allozymes with reduced activity may indicate a relatively reduced risk for development of a chemically induced cancer. Additional risk factors including, for example, family history and other genetic factors can be considered when determining risk. Predisposition to thyroid disease or cancer can be determined based on the presence or absence of a single sulfotransferase sequence variant or based on a variant profile. "Variant profile" refers to the presence or absence of a plurality (i.e., two or more sequence variants) of SULT1C1 nucleotide sequence variants or SULT1C1 amino acid sequence variants. For example, a variant profile can include the complete SULT1C1 haplotype of the mammal or can include the presence or absence of a set of common non-synonymous SNPs (i.e., single nucleotide substitutions that alter the amino acid sequence of a SULT1C1 polypeptide). In one embodiment, the variant profile includes detecting the presence or absence of three or more non-synonymous SNPs (e.g., 3, 4, 5, 6, or 7 non-synonymous SNPs and combinations thereof) described above.

Articles of Manufacture

Articles of manufacture of the invention include populations of isolated SULT1C1 nucleic acid molecules or SULT1C1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different SULT1C1 nucleic acid or SULT1C1 polypeptide sequence variant. Such articles of manufacture can include two or more sequence variants of SULT1C1, or can include all of the sequence variants known for SULT1C1. Furthermore, nucleic acid molecules containing sequence variants for other sulfotransferases, such as SULT1A1, SULT1A2, SULT1A3, and SULT1A2, can be included on the substrate. See, WO 99/64630 and WO 00/20605 for a description of other SULT1A1, SULT1A2, SULT1A3, and SULT1A2 sequence variants.

Suitable substrates can be of any shape or form and can be constructed from, for example, glass, silicon, metal, plastic, cellulose or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., *Nature Genet.*, 14:441-447 (1996); and U.S. Pat. Nos. 5,770, 722 and 5,733,729.

The invention will be further described in the following examples, which do not limit the scope of the invention described in the claims.

EXAMPLES

Example 1

Methods and Materials: PCR Amplification and DNA Sequencing:

Blood samples were obtained from 89 randomly selected Caucasian blood donors (61 women, 28 men) at the Mayo Clinic Blood Bank in Rochester, Minn. Genomic DNA was extracted from each blood sample using QIAamp Blood Kits (Qiagen, Valencia, Calif.). Once extracted, the genomic DNA was used as template for PCR with SULT1C1-specific primers. To make it possible to sequence SULT1C1, the 9 exons in the gene, including the initial untranslated exon and an alternatively-spliced exon located within intron 3 (exon 3b), were amplified from each of the 89 DNA samples by use of PCR. Specifically, PCR primers were designed that flanked the exons and that would produce amplification products 400-500 bp in length. Two overlapping amplifications were required for the first and last exons because of their lengths. Therefore, 11 separate amplifications were performed for each DNA sample. Dye primer DNA sequencing chemistry was used to facilitate the identification of heterozygous bases. To make that possible, M13 sequence tags were added to the 5' ends of each primer. Locations of primers were chosen to avoid repetitive sequence and to ensure amplification specificity. The sequences and locations of each primer within the gene are listed in Table 1. All forward primers contained the M13 forward sequence, and all reverse primers contained the M13 reverse sequence to make it possible to use dye primer DNA sequencing chemistry. "F" represents forward; "R", reverse; "U", upstream; "D", downstream; "I", intron; "FR", flanking region; and "UTR", untranslated region.

mutagenesis using the method described by Ho et al., *Gene* (1989) 77(1):51-9. Each SULT1C1 cDNA was amplified by PCR and subcloned into the EcoRI restriction site of the eukaryotic expression vector p91023(B). After subcloning, all inserts were sequenced to assure that no spurious nucleotide point mutations had been introduced during the PCR amplifications. COS-1 cells were transfected with these expression constructs by the TransFast™ reagent (Promega, Madison, Wis.) as suggested by the manufacturer (i.e., using

TABLE 1

PCR primers used for SULT1C1 resequencing

| Primer Name | Primer Location | 5'-M13 tag | - | Primer Sequence Gene Specific Primer-3' | SEQ ID NO: |
|---|---|---|---|---|---|
| UF(-807) M13 | 5'-FR | TGTAAAACGACGGCCAGT | - | GTACAATAAGGCAAAGAAAAAATAAGTACACACCTAAG | 4 |
| UR(-357) M13 | 5'-UTR | CAGGAAACAGCTATGACC | - | CACTCTACTCCTCCTCTCGGTCAC | 5 |
| UF(-405) M13 | 5'-UTR | TGTAAAACGACGGCCAGT | - | GGAAAGATGTGAAAAACTCTAGCTGGTGAC | 6 |
| I1R99 M13 | Intron 1 | CAGGAAACAGCTATGACC | - | TTTGAATAAATGCATCTGTAAAGCCACACCTATGT | 7 |
| I1F(-120) M13 | Intron 1 | TGTAAAACGACGGCCAGT | - | AATGTGAATGTACTTAATGCCTCTGAACTGTACAC | 8 |
| I2R112 M13 | Intron 2 | CAGGAAACAGCTATGACC | - | CATTGTGGAACAATAAGAAGGAGCAGGTTTC | 9 |
| I2F275 M13 | Intron 2 | TGTAAAACGACGGCCAGT | - | ATGGCAAACAGGATTCTGACCCAAGGG | 10 |
| I3R186 M13 | Intron 3 | CAGGAAACAGCTATGACC | - | GAAACATATGACAGTGAAAATGAGAGAGAAAGAGA | 11 |
| I3F(-2464) M13 | Intron 3 | TGTAAAACGACCGCCAGT | - | GCACTTTTTTTGAGACAGGGTCTCACTCTG | 12 |
| I3R(-2040) M13 | Intron 3 | CAGGAAACAGCTATGACC | - | GGGAAAAGCCCTATGAACAAGAGCTAGAAAA | 13 |
| I3F(-151) M13 | Intron 3 | TGTAAAACGACGGCCAGT | - | ATTAATAATCCCATTGTAAAATCCCAAAAGAAAGTCAAG | 14 |
| I4R155 M13 | Intron 4 | CAGGAAACAGCTATGACC | - | GCTGAATGTAGAACTTTATGTTTTCTCTTTGCTGGTA | 15 |
| I4F(-114) M13 | Intron 4 | TGTAAAACGACGGCCAGT | - | AGGGCCAGCACTGCAGAACTGAG | 16 |
| I5R155 M13 | Intron 5 | CAGGAAACAGCTATGACC | - | ACACTCAGTGGCCAGCTTGCTCTG | 17 |
| I15F313 M13 | Intron 5 | TGTAAAACGACGGCCAGT | - | CTACACCACCCTCAAAATCAAACAGATCAG | 18 |
| I6R146 M13 | Intron 6 | CAGGAAACAGCTATGACC | - | GCGGCAAGGGTAACATTGGACTGGAAT | 19 |
| I6F91 M13 | Intron 6 | TGTAAAACGACGGCCAGT | - | TGTAGTATTTCTTTATGATACTCTCATTCATTCCAGTC | 20 |
| I7R171 M13 | Intron 7 | CAGGAAACAGCTATGACC | - | CTAGAAAGCTCTCTTCTACAACAGGATCAAATC | 21 |
| I7F(-184) M13 | Intron 7 | TGTAAAACGACGGCCAGT | - | ACCGAGTCCCCTAGGCCTGCTTCTTATA | 22 |
| SULT1C1R1008 M13 | 3'-UTR | CAGGAAACAGCTATGACC | - | GTACTACATTGTATACATTCACAATATGCTTTCAGAG | 23 |
| SULT1C1F937 M13 | 3'-UTR | TGTAAAACGACGGCCAGT | - | ACTATCTTCAATCCTTCAGTCCCAGCCA | 24 |
| DR1305 M13 | 3'-FR | CAGGAAACAGCTATGACC | - | GAGTTCGGTGAATGGCCAGGACAG | 25 |

DNA sequencing was performed in the Mayo Clinic Molecular Biology Core Facility with an Applied Biosystems Model 377 DNA sequencers and BigDye™ (Perkin Elmer, Foster City, Calif.) dye primer sequencing chemistry. In all cases, both DNA strands were sequenced.

DNA sequence analysis: The PolyPhred 3.0 and Consed 8.0 programs were used to analyze the DNA sequence chromatograms for polymorphic sites. Each chromatogram was also analyzed visually, independent of the PolyPhred analysis, and polymorphism "calls" from these two independent analyses were compared. The University of Wisconsin GCG software package, Version 10, was also used to analyze nucleotide sequence.

COS-1 Cell Expression: Nine different SULT1C1 expression constructs were made using the p91023(B) expression vector. See, Wong et al., *Science* (1985) 228:810-815, for a description of the p91023(B) vector. Eight of the constructs were designed to express variant SULT1C1 polypeptides, while the remaining construct was designed to express a wild type SULT1C1. All SULT1C1 cDNA sequences used to create the expression constructs were created by site directed a 1:1 charge ratio). As a control, a transfection was also performed with "empty" p91023(B), i.e., vector lacking an insert, to make it possible to correct for endogenous COS-1 cell SULT activity. The control plasmid pSV-β-galactosidase (Promega, Madison, Wis.) was cotransfected with each SULT1C1 construct to make it possible to correct for transfection efficiency. Two independent transfections, each consisting of three separate plates, were performed with each of the expression constructs. After 48 hours in culture, the transfected cells were harvested and high speed supernatant (HSS) cytosol preparations were prepared as described by Wood, T. C. et al., *Biochem. Biophys. Res. Commun.*, 198:1119-1127 (1994). Aliquots of these cytosol preparations were stored at −80° C. prior to assay.

Enzyme Assays: β-galactosidase activity in each of the COS-1 HSS preparations was measured with the β-galactosidase Enzyme Assay System (Promega, Madison, Wis.). SULT1C1 enzyme activity was measured with an assay that involves sulfate conjugation of a sulfate acceptor substrate, 4-nitrophenol (4-NP), in the presence of $[^{35}S]$-3'-phosphoadenosine-5'-phosphosulfate (PAPS), the sulfate donor for the reaction. See, Campbell, N. R. C. et al., *Biochem. Pharmacol.*, 36:1435-1446 (1987). The HSS preparations of recombinant SULT1C1 variant proteins described above were used for the activity studies without any further purification. The protein concentration of each recombinant protein preparation was determined by the dye-binding method of Bradford with bovine serum albumin (BSA) as a standard. Briefly, 0.4 µM $^{35}$S-PAPS was used as the sulfate donor with 10 mM 4-NP as the sulfate acceptor substrate in 5 mM potassium phosphate buffer at pH 7.4. Blanks were samples that did not contain 4-NP. Cytosol from COS-1 cells that had been transfected with empty p91023(B) was used to correct for endogenous SULT activity. Because SULTs display profound substrate inhibition, 4-NP concentrations that ranged from 100 µM to 10 mM were tested with each recombinant allozyme to ensure that the assays were performed at 4-NP concentrations that yielded maximal activity for that allozyme. Enzyme activity was expressed as nanomoles (nmoles) of sulfate conjugated product formed per hour of incubation. Apparent $K_m$ values for PAPS were determined in the presence of 10 mM 4-NP with six PAPS concentrations that varied from 0.0625 µM to 2 µM. As described subsequently, it was not possible to determine apparent $K_m$ values for 4-NP.

Data Analysis: Apparent $K_m$ values were calculated by using the method of Wilkinson with a computer program written by Cleland. Wilkinson, G. N., *Biochem. J.*, 80:324-332 (1961); and Cleland, W. W., *Nature*, 198:463-365 (1963). Statistical comparisons of data were performed by ANOVA with the StatView program, version 4.5 (Abacus Concepts, Inc., Berkeley, Calif.).

Western blot analysis: Quantitative Western blot analysis was performed with recombinant SULT1C1 protein. The quantity of cytosol loaded on the gel for each allozyme was adjusted so that each lane contained an equal quantity of β-galactosidase activity, i.e. gel loading was corrected for variation in transfection efficiency. Properties of the antibody used to detect the SULT1C1 protein have been described elsewhere. Bound antibody was detected by use of the ECL system (Amersham Pharmacia, Piscataway, N.J.). The Ambis densitometric system was used to quantitate immunoreactive protein in each lane, and those data were expressed as a percent of the intensity of the control wild type SULT1C1 protein band on that gel.

Example 2

SULT1C1 Polymorphisms

Eleven separate SULT1C1 PCR amplifications were performed for each of the 89 individual human genomic DNA samples studied. These reactions generated a total of approximately 900,000 bp of sequence. This sequence was analyzed both visually and by use of the PolyPhred software. These two analyses were performed by separate, independent observers. There were only three discrepancies in the polymorphism calls between the two methods. Two of these differences were the result of homozygous, single nucleotide sequence alterations present in single samples (at positions −760 and 599), which PolyPhred identified as differences from the consensus sequence. The third discrepancy involved a single heterozygous SNP at cDNA ORF nucleotide position 577 that was not called by PolyPhred. Therefore, the software had an advantage over a trained observer for the detection of homozygous variant sequences that might not be noticed as a result of variance in peak height, but it occasionally failed to call heterozygous variants. In addition, the software was not ideal for the evaluation of large insertion/deletion events such as the 30 bp insertion/deletion that was observed in SULT1C1 intron 3. Of the sequence analyzed, 92.9% was sequenced on both strands, making it possible to use data from the opposite strand to verify polymorphism calls. The most common reason for failure to sequence both strands was the presence of insertion/deletion events. All sequences were compared to the SULT1C1 gene sequences of GenBank accession numbers AF186257 to AF186262.

Sequencing of the 5' and 3' untranslated sequences, exons, and introns of the SULT1C1 nucleic acid revealed 31 variations, including 26 single nucleotide polymorphisms (SNPs), three insertions, and two deletions in SULT1C1 nucleic acid sequences (Table 2). Polymorphisms in exons, untranslated regions (UTR), and flanking regions (FR) are numbered relative to the adenine in the SULT1C1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1). Asterisks indicate insertions or deletions. For the 5 insertions/deletions, alleles that lack the inserted sequence are denoted by a dash. I3(107) is a 30 bp deletion, denoted by "Ins" in the wild type sequence column. The insertions at −149, I3(−2377), and I7(−101) each involve a single nucleotide. The inserted nucleotide constitutes the variant in all three cases. The deletion at I3(61-62) involves a dinucleotide (CT) that is present in the wild type sequence and absent in the variant sequence. The deletion at I3(107) involves a 30 nucleotide fragment (5'-TCTCTCCTTC-CTCTTTTCTCTCTCCCTCCC-3'; SEQ ID NO: 3) that is present in the wild type sequence and absent in the variant sequence. Seven of the 26 SNPs altered the encoded amino acid (i.e., a non-synonymous SNP), resulting in seven different single variant SULT1C1 allozymes and one double variant SULT1C1 allozyme.

The SULT1C1 cDNA sequence was used to search the EST database, and the 39 EST sequences identified were screened for the presence of the polymorphisms observed during the resequencing experiments. Only the initial 400 bp of each EST sequence was used for this comparison to assume sequence quality. None of the 7 nonsynonymous cSNPs were observed in these EST sequences. Polymorphisms that were observed only once (one allele out of the 178 sequenced) accounted for 14 of the 31 observed polymorphism. An additional 6 polymorphisms were observed twice (2 as homozygous and 4 as heterozygous samples). The average number of polymorphisms present both in the gene overall and within the ORF was 7.9 per kb sequenced (Table 3). For purposes of comparison, Table 3 also includes data from a large study of polymorphism frequencies in 74 human genes (Halushka et al., *Nat. Genet.* (1999) 22(3):239-247). Because Halushka et al. studied a slightly smaller number of samples (74 versus the 89 described), low frequency polymorphisms that would not have been detected by Halushka et al. have been eliminated because of their lower sample number. The genetic variation present within the SULT1C1 sequence was very similar to average values observed in the 74 genes sequenced by Halushka et al. The data in Table 3 also are presented by gene region, with "UTR" representing exons encoding cDNA untranslated regions and "FR" representing both 5'- and 3'-flanking regions.

TABLE 2

Human SULT1C1 polymorphisms and frequencies

| Polymorphism Position | Location In Gene | WT Sequence Nucleotide | Variant Sequence Nucleotide | Frequency |
|---|---|---|---|---|
| −760 | 5'-FR | T | G | 0.011 |
| −547 | 5'-FR | A | G | 0.006 |
| −518 | 5'-FR | C | T | 0.382 |
| −500 | 5'-FR | T | C | 0.208 |
| −258 | 5'-UTR | C | T | 0.011 |
| −149* | 5'-UTR | — | C | 0.022 |
| I1(37) | Intron 1 | T | C | 0.006 |
| 179 | Exon 3 | A | C | 0.011 |
| 218 | Exon 3 | G | A | 0.011 |
| I3(61-62)* | Intron 3 | CT | — | 0.006 |
| I3(107)* | Intron 3 | Ins/Ins | — | 0.416 |
| I3(−2377) | Intron 3 | — | T | 0.374 |
| I3(−2177) | Exon 3b | C | T | 0.006 |
| I3(−2158) | Intron 3 | C | T | 0.420 |
| I3(−80) | Intron 3 | G | A | 0.062 |
| 332 | Exon 4 | C | T | 0.006 |
| I4(68) | Intron 4 | C | A | 0.006 |
| I4(94) | Intron 4 | T | C | 0.006 |
| I4(−20) | Intron 4 | C | T | 0.045 |
| I5(97) | Intron 5 | T | A | 0.006 |
| 577 | Exon 6 | T | C | 0.006 |
| I6(73) | Intron 6 | A | G | 0.062 |
| 599 | Exon 7 | A | T | 0.011 |
| 715 | Exon 7 | A | G | 0.006 |
| 763 | Exon 7 | T | G | 0.067 |
| I7(−101)* | Intron 7 | — | A | 0.011 |
| 1027 | 3'-UTR | T | C | 0.006 |
| 1191 | 3'-FR | A | G | 0.073 |
| 1217 | 3'-FR | A | G | 0.006 |
| 1251 | 3'-FR | A | G | 0.006 |
| 1260 | 3'-FR | T | C | 0.006 |

TABLE 3

SULT1C1 polymorphism frequencies

Polymorphisms per kb

| | SULT1C1 | | |
|---|---|---|---|
| | Complete Data | Corrected | 74 Human Genes |
| Gene(s) | 1 | 1 | 74 |
| Samples | 89 | 89 | 75 |
| Min. Allele Freq. | 0.56% | 0.68% | 0.68% |
| Overall | 7.9 | 4.3 | 4.6 |
| Coding | 7.9 | 4.5 | 4.4 |
| Noncoding | 7.9 | 4.3 | 5.9 |
| UTR and FR | 9.5 | 5.2 | 4.4 |
| Introns | 6.9 | 3.7 | 6.0 |

The DNA samples used in these studies were obtained only from Caucasian subjects. Therefore, allele frequencies for these polymorphisms in a Caucasian population sample were calculated. Chi-square analysis indicated no significant gender-dependent differences in allele frequencies for any of the SULT1C1 polymorphisms found. The lowest allele frequency that was possible to detect was 0.56% since 89 DNA samples (178 alleles) were used. Those frequencies are also listed in Table 2. Overall, 17 of the 31 polymorphisms had allele frequencies greater than 1% and, as a result, may be considered "common" in the population sample. Five of the polymorphisms had allele frequencies greater than 10%. A total of eight SNPs were observed in the SULT1C1 coding region (FIG. 1 and Table 2), and only one of those cSNPs was synonymous (i.e., no change in amino acid sequence). This single synonymous cSNP was located in exon 3b, an exon that results from alternative splicing and is only rarely represented in mRNA. The other 7 cSNPs, all located in the exons that encode the wild type SULT1C1 protein, were nonsynonymous. Three of those nonsynonymous cSNPs were observed only once, 3 were seen twice and had allele frequencies of 1.1%, and one was present in 12 alleles, with a frequency of 6.7%. This common variant was T763G, designated SULT1C1*2, resulted in a Ser255Ala alteration in the encoded amino acid sequence. In addition to SNPs, 5 insertions/deletions were observed in SULT1C1 (FIG. 1 and Table 2). Three of those polymorphisms involved single bases, one was a two base change, and one consisted of a common 30 bp insertion/deletion in intron 3 that contained two 15 bp repeats. All of the allele frequencies for polymorphisms identified during the resequencing experiments, with two exceptions, conformed to the predictions of the Hardy-Weinberg theorum when the exact test was used (threshold p<0.05). Those two exceptions involved SNPs (−760 and 599), each of which was observed only as a homozygous change in a single sample. Studies of genetic polymorphisms are moving increasingly beyond merely dealing with single SNPs to also address the issue of haplotype, the combination of polymorphisms present within each allele. Therefore, linkage disequilibrium between individual polymorphisms was performed, along with common SULT1C1 haplotype analysis.

Example 3

Linkage Disequilibrium and Haplotype Analysis

Linkage disequilibrium analysis was performed after all of the DNA samples had been genotyped at each of the 31 polymorphic sites. The 10 polymorphisms with allele frequencies greater than 2.5% were chosen for inclusion in this analysis, since there was inadequate statistical power for the analysis of less common polymorphisms. All possible pairwise combinations of these 10 polymorphisms were tested for linkage disequilibrium using the EH program developed by Terwilliger and Ott, *Handbook of Human Genetic Linkage*, The Johns Hopkins University Press, Baltimore, pp. 188-193 (1994). The output of this program was used to calculate d' values, a method for reporting linkage data that is independent of sample size (Table 4). The genotype data were also used for haplotype analysis. In this case, unambiguous haplotype assignment could be made for samples that contained no more than one heterozygous locus. Haplotypes for some of the remaining alleles were inferred from the genotype data as well as the EM probabilities (Table 5).

TABLE 4

SULT1C1 linkage disequilibrium analysis

| Polymorphism Pair | | d' Value | $\chi^2$ Value |
|---|---|---|---|
| −518 | I3(107)* | −0.843 | 34.22 |
| I3(107)* | I3(−2377) | 0.852 | 34.05 |
| I3(−2158) | I4(−20) | 1.000 | 8.84 |
| I3(−80) | I6(73) | 0.903 | 51.15 |
| I3(−80) | 763 | 0.902 | 48.45 |
| I3(−80) | 1191 | 0.900 | 45.24 |
| I6(73) | 763 | 1.000 | 61.80 |
| I6(73) | 1191 | 1.000 | 57.53 |
| 763 | 1191 | 0.909 | 52.07 |

TABLE 5

SULT1C1 haplotype analysis

| Name | Haplotype |
|---|---|
| A | I3(−2377) |
| B | −518, −500, I3(107) |
| C | −518, I3(107), I3(−2158) |
| D | I3(−2158) |
| E | I3(107), I3(−2158) |
| F | −518, I3(−2158) |
| G | I3(−2158), I4(−20) |
| H | I3(107), I3(−2158), I4(−20) |
| I | I3(107), I3(−2377) |
| J | −760, −500, I3(−2377) |
| K | −760, I3(−2377) |
| L | −518, I1(37), I3(107), I3(−2158) |
| M | I3(−2377), 1260 |
| N | 599,715 |
| O | 179,763 |
| P | 218,763 |

Example 4

Activity of SULT1C1 Allozymes

Cytosol preparations of recombinant SULT1C1 allozymes, were used to assess catalytic activities as described in Example 1. Resulting activities were adjusted to a percentage of the wild type SULT1C1 enzyme activity. The PAPS apparent $K_m$ values varied 7-fold, and seven of the eight enzymes exhibit reduced enzyme activity relative to the wild type SULT1C1 enzyme (Table 6).

TABLE 6

Recombinant human SULT1C1 biochemical properties

| Polymorphism | Amino Acid Change | % WT activity | Apparent $K_m$ |
|---|---|---|---|
| A179C | Asp60Ala | 13.9 ± 0.3 | 4.00 ± 0.47 |
| G218A | Arg73Gln | 14.5 ± 1.9 | 0.57 ± 0.15 |
| C332T | Ser111Phe | 0 | N.D. |
| T577C | Phe193Leu | 39.3 ± 1.4 | 2.95 ± 0.27 |
| A599T | Asp200Val | 48.1 ± 4.2 | 1.20 ± 0.12 |
| A715G | Thr239Ala | 52.6 ± 1.7 | 1.14 ± 0.11 |
| T763G | Ser255Ala | 98.9 ± 5.9 | 0.56 ± 0.06 |
| A599T/ A715G | Asp200Val/ Thr239Ala | 49.3 ± 2.8 | 1.82 ± 0.14 |
| wild type | none | 100 | 0.77 ± 0.04 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for obtaining a SULT1C1 variant profile, wherein said method comprises:
   a) providing a biological sample from a human, and
   b) detecting the presence or absence of a plurality of SULT1C1 nucleotide sequence variants in said sample to obtain a variant profile of said human, wherein said nucleotide sequence variants are at positions selected from the group consisting of nucleotide 179 of SEQ ID NO:26, nucleotide 218 of SEQ ID NO:26, nucleotide 332 of SEQ ID NO:26, and nucleotide 763 of SEQ ID NO:26.

2. The method of claim 1, wherein said method further comprises communicating said profile to a medical or research professional.

3. A method for determining the thyroid hormone or 4-nitrophenol sulfonator status of a human subject, said method comprising testing said subject to determine whether said subject comprises a variant SULT1C1 nucleic acid that comprises a nucleotide sequence variant at a position selected from the group consisting of nucleotide 179 of SEQ ID NO:26, nucleotide 218 of SEQ ID NO:26, nucleotide 332 of SEQ ID NO:26, and nucleotide 763 of SEQ ID NO:26.

4. The method of claim 3, wherein said variant SULT1C1 nucleic acid comprises a cytosine at position 179 of SEQ ID NO:26.

5. The method of claim 3, wherein said variant SULT1C1 nucleic acid comprises a cytosine at position 218 of SEQ ID NO:26.

6. The method of claim 3, wherein said variant SULT1C1 nucleic acid comprises a guanine at position 332 of SEQ ID NO:26.

7. The method of claim 3, wherein said variant SULT1C1 nucleic acid comprises a guanine at position 763 of SEQ ID NO:26.

8. The method of claim 3, wherein said determining comprises:
   wherein said method comprises:
   a) providing a biological sample from said subject, and
   b) detecting the presence or absence of said SULT1C1 nucleotide sequence variant in said sample.

* * * * *

UNITED STATES PATENT AND TRADEMARK OFFICE
CERTIFICATE OF CORRECTION

PATENT NO.         : 7,541,169 B2
APPLICATION NO. : 11/348099
DATED               : June 2, 2009
INVENTOR(S)       : Richard M. Weinshilboum Page 1 of 1

It is certified that error appears in the above-identified patent and that said Letters Patent is hereby corrected as shown below:

Title Page Item (73), Assignee, please delete "NY" and insert --MN-- therefor;

Title Page Item (56), References Cited, Other Publications, Hacia et al. reference, please delete "BRCAI" and insert --BRCA1-- therefor;

Title Page Item (56), References Cited, Other Publications, Halushka et al. reference, please delete "sinle" and insert --single-- therefor;

Title Page Item (56), References Cited, Other Publications, Sakakibara et al. reference, please delete "SULTIC" and insert --SULT1C-- therefor;

Column 48, line 61 (Claim 8), please delete "SULT1C1nucleotide" and insert --SULT1C1 nucleotide -- therefor.

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,541,169 B2
APPLICATION NO. : 11/348099
DATED : June 2, 2009
INVENTOR(S) : Freimuth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this

Fourteenth Day of December, 2010

David J. Kappos
*Director of the United States Patent and Trademark Office*

SEQUENCE LISTING

<160> NUMBER OF SEQ ID NOS: 37

<210> SEQ ID NO 1
<211> LENGTH: 1380
<212> TYPE: DNA
<213> ORGANISM: Homo sapiens

<400> SEQUENCE: 1

```
tccagcctgg gcaacaggag tgaaacacca tctcaaaaaa aaaaaaaaaa aagaaaaaag      60
aaagaaaaag aaagttcaat ttattgggaa aaaaagagcc ctttggaaac aaggaggaag     120
aagaagtgtc ggcaaagaag cattaggagg ttcagggtca aagaagacaa ggaaagcttt     180
ggcaagaagg gcagatgggg tgcagaatta tgcttcaatt ccagaaagga aagcactggg     240
gtagatacaa ggttggggct ggcagaagag tagcagttca gagatcatta acacttgatc     300
catttaattt cccaggtaac caaagacacc atggaatata atctgcctcc actaaagtgt     360 acctttgta caataaggca aagaaaaaat aagtacacac ctaagctcta gacttttgtt     420
ctatcctctc tgcattttcg gtgtggatga atacaacttg ggaagaaagg aaagaagaac     480
cagcagtttt aagcacttac tatttgctct gcaaagtgta ttcatcaaca ttgttgcttt     540
caatcttaaa gcatggattg gagacaggca gtattacccca cacttcatag atgcagaaat     600
taaatctcag gctaaggagg aaggaaaagg gagttcacca aataagcagg agcctacctg     660
aagcctgatg catctggtcc tagagccaac cttccatttc cccccagccc ccacctgttt     720
aagcttcgag gccagtggga ggagggaggg gccaggcagc tgagggccag gaaagatgtg     780
aaaaactcta gctggtgacc gagaggagga gtagagtgtg cccttagttc atatgaacta     840
gagggagttg gtatttgcac agcagtcagg gtcacatgag tgatcatggt acagtgagaa     900
gttctccctc ccagggccag gtcacagggt ttgtttctgt tcaatccgga ttcttccagt     960
```

-continued

```
aaaagcttca acttcccaca ctgaagctga gagcctccca aagtgctggc tacctgctga   1020
gcgcccccgt aactctgaca cagtagtaat ttgagcctct gcaattgccg tctgcttcct   1080
gtgaaagtcc tttccgtgcc cactgaccct tgagtgggcc tttgagctgc tgactttcag   1140
ctggaacttg aaggtaagaa tatggcttaa agaaattct gtacctaact cgttaattta    1200
ttttttaacc tttagccaca taggtgtggc tttacagatg catttattca aaccagaaaa   1260
gatcctaaga atctgataaa ataatataaa agagttttgt taacagcctc cagcctaaaa   1320
attcagacct agaaattcag gacccccctc aaatcacctc caaaagctct ctctcctgta   1380
```

<210> SEQ ID NO 2
<211> LENGTH: 296
<212> TYPE: PRT
<213> ORGANISM: Homo sapiens

<400> SEQUENCE: 2

```
Met Ala Leu Thr Ser Asp Leu Gly Lys Gln Ile Lys Leu Lys Glu Val
  1               5                  10                  15

Glu Gly Thr Leu Leu Gln Pro Ala Thr Val Asp Asn Trp Ser Gln Ile
             20                  25                  30

Gln Ser Phe Glu Ala Lys Pro Asp Asp Leu Leu Ile Cys Thr Tyr Pro
         35                  40                  45

Lys Ala Gly Thr Thr Trp Ile Gln Glu Ile Val Asp Met Ile Glu Gln
     50                  55                  60

Asn Gly Asp Val Glu Lys Cys Gln Arg Ala Ile Ile Gln His Arg His
 65                  70                  75                  80

Pro Phe Ile Glu Trp Ala Arg Pro Pro Gln Pro Ser Gly Val Glu Lys
                 85                  90                  95

Ala Lys Ala Met Pro Ser Pro Arg Ile Leu Lys Thr His Leu Ser Thr
            100                 105                 110

Gln Leu Leu Pro Pro Ser Phe Trp Glu Asn Asn Cys Lys Phe Leu Tyr
        115                 120                 125

Val Ala Arg Asn Ala Lys Asp Cys Met Val Ser Tyr Tyr His Phe Gln
    130                 135                 140

Arg Met Asn His Met Leu Pro Asp Pro Gly Thr Trp Glu Glu Tyr Phe
145                 150                 155                 160

Glu Thr Phe Ile Asn Gly Lys Val Val Trp Gly Ser Trp Phe Asp His
                165                 170                 175

Val Lys Gly Trp Trp Glu Met Lys Asp Arg His Gln Ile Leu Phe Leu
            180                 185                 190

Phe Tyr Glu Asp Ile Lys Arg Asp Pro Lys His Glu Ile Arg Lys Val
        195                 200                 205

Met Gln Phe Met Gly Lys Lys Val Asp Glu Thr Val Leu Asp Lys Ile
    210                 215                 220

Val Gln Glu Thr Ser Phe Glu Lys Met Lys Glu Asn Pro Met Thr Asn
225                 230                 235                 240

Arg Ser Thr Val Ser Lys Ser Ile Leu Asp Gln Ser Ile Ser Ser Phe
                245                 250                 255

Met Arg Lys Gly Thr Val Gly Asp Trp Lys Asn His Phe Thr Val Ala
            260                 265                 270

Gln Asn Glu Arg Phe Asp Glu Ile Tyr Arg Arg Lys Met Glu Gly Thr
        275                 280                 285

Ser Ile Asn Phe Cys Met Glu Leu
    290                 295
```

<210> SEQ ID NO 3
<211> LENGTH: 30
<212> TYPE: DNA
<213> ORGANISM: Homo sapiens

<400> SEQUENCE: 3
tctctccttc ctcttttctc tctccctccc                               30

<210> SEQ ID NO 4
<211> LENGTH: 56
<212> TYPE: DNA
<213> ORGANISM: Artificial Sequence
<220> FEATURE:
<223> OTHER INFORMATION: primer for PCR

<400> SEQUENCE: 4
tgtaaaacga cggccagtgt acaataaggc aaagaaaaaa taagtacaca cctaag      56

<210> SEQ ID NO 5
<211> LENGTH: 42
<212> TYPE: DNA
<213> ORGANISM: Artificial Sequence
<220> FEATURE:
<223> OTHER INFORMATION: primer for PCR

<400> SEQUENCE: 5
caggaaacag ctatgaccca ctctactcct cctctcggtc ac                  42

<210> SEQ ID NO 6
<211> LENGTH: 48
<212> TYPE: DNA
<213> ORGANISM: Artificial Sequence
<220> FEATURE:
<223> OTHER INFORMATION: primer for PCR

<400> SEQUENCE: 6
tgtaaaacga cggccagtgg aaagatgtga aaaactctag ctggtgac            48

<210> SEQ ID NO 7
<211> LENGTH: 53
<212> TYPE: DNA
<213> ORGANISM: Artificial Sequence
<220> FEATURE:
<223> OTHER INFORMATION: primer for PCR

<400> SEQUENCE: 7
caggaaacag ctatgacctt tgaataaatg catctgtaaa gccacaccta tgt       53

<210> SEQ ID NO 8
<211> LENGTH: 53
<212> TYPE: DNA
<213> ORGANISM: Artificial Sequence
<220> FEATURE:
<223> OTHER INFORMATION: primer for PCR

<400> SEQUENCE: 8
tgtaaaacga cggccagtaa tgtgaatgta cttaatgcct ctgaactgta cac       53

<210> SEQ ID NO 9
<211> LENGTH: 49
<212> TYPE: DNA
<213> ORGANISM: Artificial Sequence
<220> FEATURE:
<223> OTHER INFORMATION: primer for PCR

```
<400> SEQUENCE: 9
caggaaacag ctatgaccca ttgtggaaca ataagaagga gcaggtttc          49

<210> SEQ ID NO 10
<211> LENGTH: 45
<212> TYPE: DNA
<213> ORGANISM: Artificial Sequence
<220> FEATURE:
<223> OTHER INFORMATION: primer for PCR

<400> SEQUENCE: 10
tgtaaaacga cggccagtat ggcaaacagg attctgaccc aaggg              45

<210> SEQ ID NO 11
<211> LENGTH: 53
<212> TYPE: DNA
<213> ORGANISM: Artificial Sequence
<220> FEATURE:
<223> OTHER INFORMATION: primer for PCR

<400> SEQUENCE: 11
caggaaacag ctatgaccga acatatgac agtgaaaatg agagagaaag aga       53

<210> SEQ ID NO 12
<211> LENGTH: 49
<212> TYPE: DNA
<213> ORGANISM: Artificial Sequence
<220> FEATURE:
<223> OTHER INFORMATION: primer for PCR

<400> SEQUENCE: 12
tgtaaaacga cggccagtgc actttttttt gagacagggt ctcactctg          49

<210> SEQ ID NO 13
<211> LENGTH: 49
<212> TYPE: DNA
<213> ORGANISM: Artificial Sequence
<220> FEATURE:
<223> OTHER INFORMATION: primer for PCR

<400> SEQUENCE: 13
caggaaacag ctatgaccgg gaaaagccct atgaacaaga gctagaaaa          49

<210> SEQ ID NO 14
<211> LENGTH: 57
<212> TYPE: DNA
<213> ORGANISM: Artificial Sequence
<220> FEATURE:
<223> OTHER INFORMATION: primer for PCR

<400> SEQUENCE: 14
tgtaaaacga cggccagtat taataatccc attgtaaaat cccaaaagaa agtcaag  57

<210> SEQ ID NO 15
<211> LENGTH: 55
<212> TYPE: DNA
<213> ORGANISM: Artificial Sequence
<220> FEATURE:
<223> OTHER INFORMATION: primer for PCR

<400> SEQUENCE: 15
caggaaacag ctatgaccgc tgaatgtaga actttatgtt ttctctttgc tggta    55

<210> SEQ ID NO 16
<211> LENGTH: 41
```

```
<212> TYPE: DNA
<213> ORGANISM: Artificial Sequence
<220> FEATURE:
<223> OTHER INFORMATION: primer for PCR

<400> SEQUENCE: 16
tgtaaaacga cggccagtag ggccagcact gcagaactga g                    41

<210> SEQ ID NO 17
<211> LENGTH: 42
<212> TYPE: DNA
<213> ORGANISM: Artificial Sequence
<220> FEATURE:
<223> OTHER INFORMATION: primer for PCR

<400> SEQUENCE: 17
caggaaacag ctatgaccac actcagtggc cagcttgctc tg                   42

<210> SEQ ID NO 18
<211> LENGTH: 48
<212> TYPE: DNA
<213> ORGANISM: Artificial Sequence
<220> FEATURE:
<223> OTHER INFORMATION: primer for PCR

<400> SEQUENCE: 18
tgtaaaacga cggccagtct acaccaccct caaaatcaaa cagatcag              48

<210> SEQ ID NO 19
<211> LENGTH: 45
<212> TYPE: DNA
<213> ORGANISM: Artificial Sequence
<220> FEATURE:
<223> OTHER INFORMATION: primer for PCR

<400> SEQUENCE: 19
caggaaacag ctatgaccgc ggcaagggta acattggact ggaat                 45

<210> SEQ ID NO 20
<211> LENGTH: 56
<212> TYPE: DNA
<213> ORGANISM: Artificial Sequence
<220> FEATURE:
<223> OTHER INFORMATION: primer for PCR

<400> SEQUENCE: 20
tgtaaaacga cggccagttg tagtatttct ttatgatact ctcattcatt ccagtc     56

<210> SEQ ID NO 21
<211> LENGTH: 51
<212> TYPE: DNA
<213> ORGANISM: Artificial Sequence
<220> FEATURE:
<223> OTHER INFORMATION: primer for PCR

<400> SEQUENCE: 21
caggaaacag ctatgaccct agaaagctct cttctacaac aggatcaaat c          51

<210> SEQ ID NO 22
<211> LENGTH: 46
<212> TYPE: DNA
<213> ORGANISM: Artificial Sequence
<220> FEATURE:
<223> OTHER INFORMATION: primer for PCR

<400> SEQUENCE: 22
```

-continued

<210> SEQ ID NO 23
<211> LENGTH: 55
<212> TYPE: DNA
<213> ORGANISM: Artificial Sequence
<220> FEATURE:
<223> OTHER INFORMATION: primer for PCR

<400> SEQUENCE: 23
caggaaacag ctatgaccgt actacattgt atacattcac aatatgcttt cagag    55

<210> SEQ ID NO 24
<211> LENGTH: 46
<212> TYPE: DNA
<213> ORGANISM: Artificial Sequence
<220> FEATURE:
<223> OTHER INFORMATION: primer for PCR

<400> SEQUENCE: 24
tgtaaaacga cggccagtac tatcttcaat ccttcagtcc cagcca    46

<210> SEQ ID NO 25
<211> LENGTH: 42
<212> TYPE: DNA
<213> ORGANISM: Artificial Sequence
<220> FEATURE:
<223> OTHER INFORMATION: primer for PCR

<400> SEQUENCE: 25
caggaaacag ctatgaccga gttcggtgaa tggccaggac ag    42

<210> SEQ ID NO 26
<211> LENGTH: 891
<212> TYPE: DNA
<213> ORGANISM: Homo sapiens
<220> FEATURE:
<221> NAME/KEY: CDS
<222> LOCATION: (1)...(888)

<400> SEQUENCE: 26

| atg gcc ctg acc tca gac ctg ggg aaa cag ata aaa ctg aaa gag gtg | 48 |
| Met Ala Leu Thr Ser Asp Leu Gly Lys Gln Ile Lys Leu Lys Glu Val | |
| 1               5                   10                  15     | |

| gag ggg acc ctc ctg cag cct gca act gtg gac aac tgg agc cag atc | 96 |
| Glu Gly Thr Leu Leu Gln Pro Ala Thr Val Asp Asn Trp Ser Gln Ile | |
|                 20                  25                  30     | |

| cag agc ttc gag gcc aaa cca gat gat ctc ctc atc tgc acc tac cct | 144 |
| Gln Ser Phe Glu Ala Lys Pro Asp Asp Leu Leu Ile Cys Thr Tyr Pro | |
|         35                  40                  45             | |

| aaa gca ggg aca acg tgg att cag gaa att gtg gat atg att gaa cag | 192 |
| Lys Ala Gly Thr Thr Trp Ile Gln Glu Ile Val Asp Met Ile Glu Gln | |
|     50                  55                  60                 | |

| aat ggg gac gtg gag aag tgc cag cga gcc atc atc caa cac cgc cat | 240 |
| Asn Gly Asp Val Glu Lys Cys Gln Arg Ala Ile Ile Gln His Arg His | |
| 65                  70                  75                  80 | |

| cct ttc att gag tgg gct cgg cca ccc caa cct tct ggt gtg gaa aaa | 288 |
| Pro Phe Ile Glu Trp Ala Arg Pro Pro Gln Pro Ser Gly Val Glu Lys | |
|                 85                  90                  95     | |

| gcc aaa gca atg ccc tct cca cgg ata cta aag act cac ctt tcc act | 336 |
| Ala Lys Ala Met Pro Ser Pro Arg Ile Leu Lys Thr His Leu Ser Thr | |
|             100                 105                 110        | |

| cag ctg ctg cca ccg tct ttc tgg gaa aac aac tgc aag ttc ctt tat | 384 |
| Gln Leu Leu Pro Pro Ser Phe Trp Glu Asn Asn Cys Lys Phe Leu Tyr | |

```
                      115                   120                   125
gta gct cga aat gcc aaa gac tgt atg gtt tcc tac tac cat ttc caa       432
Val Ala Arg Asn Ala Lys Asp Cys Met Val Ser Tyr Tyr His Phe Gln
    130                 135                 140 agg atg aac cac atg ctt cct gac cct ggt acc tgg gaa gag tat ttt       480
Arg Met Asn His Met Leu Pro Asp Pro Gly Thr Trp Glu Glu Tyr Phe
145                 150                 155                 160 gaa acc ttc atc aat gga aaa gtg gtt tgg ggt tcc tgg ttt gac cac       528
Glu Thr Phe Ile Asn Gly Lys Val Val Trp Gly Ser Trp Phe Asp His
                    165                 170                 175 gtg aaa gga tgg tgg gag atg aaa gac aga cac cag att ctc ttc ctc       576
Val Lys Gly Trp Trp Glu Met Lys Asp Arg His Gln Ile Leu Phe Leu
                180                 185                 190 ttc tat gag gac ata aag agg gac cca aag cat gaa att cgg aag gtg       624
Phe Tyr Glu Asp Ile Lys Arg Asp Pro Lys His Glu Ile Arg Lys Val
            195                 200                 205 atg cag ttc atg gga aag aag gtg gat gaa aca gtg cta gat aaa att       672
Met Gln Phe Met Gly Lys Lys Val Asp Glu Thr Val Leu Asp Lys Ile
        210                 215                 220 gtc cag gag acg tca ttt gag aaa atg aaa gaa aat ccc atg aca aat       720
Val Gln Glu Thr Ser Phe Glu Lys Met Lys Glu Asn Pro Met Thr Asn
225                 230                 235                 240 cgt tct aca gtt tcc aaa tct atc ttg gac cag tca att tcc tcc ttc       768
Arg Ser Thr Val Ser Lys Ser Ile Leu Asp Gln Ser Ile Ser Ser Phe
                    245                 250                 255 atg aga aaa gga act gtg ggg gat tgg aaa aac cac ttc act gtt gcc       816
Met Arg Lys Gly Thr Val Gly Asp Trp Lys Asn His Phe Thr Val Ala
                260                 265                 270 cag aat gag agg ttt gat gaa atc tat aga aga aag atg gaa gga acc       864
Gln Asn Glu Arg Phe Asp Glu Ile Tyr Arg Arg Lys Met Glu Gly Thr
            275                 280                 285 tcc ata aac ttc tgc atg gaa ctc tga                                    891
Ser Ile Asn Phe Cys Met Glu Leu
        290                 295

<210> SEQ ID NO 27
<211> LENGTH: 1087
<212> TYPE: DNA
<213> ORGANISM: Homo sapiens

<400> SEQUENCE: 27
tttcccatag ggaccccaac cctgagacac tatggccctg acctcagacc tggggaaaca      60
gataaaactg aaagaggtgg aggggaccct cctgcagcct gcaactgtgg acaactggag     120
ccagatccag agcttcgagg ccaaaccaga tgatctcctc atctgcacct accctaaagc     180
aggtgattgc agggtaggag ggacagcaaa gacctgctga gccagcacag gctcatcact     240
taagttagaa ttccccttct taggaaacct gctccttctt attgttccac aatgggtttt     300
ggagctcagg gctcacacag gatgcctgat atccgagttt ccaggaaaag ctgctatgct     360
ctaccatgca ctggtcttgg gtggagagac ccttgcctgt gctgctccac tccctacaga     420
gatccaaagt ccatccctca tggacttcta tcactcatgg caaacaggat tctgacccaa     480
ggggagggtg atgcaaacac caaggctcta catcctcttc gtttactcgg gactcttcag     540
ggaagattgt ctaacagatt tctgcttctc atccttcctt tctgagcctc agggacaacg     600
tggattcagg aaattgtgga tatgattgaa cagaatgggg acgtggagaa gtgccagcga     660
gccatcatcc aacaccgcca tcctttcatt gagtgggctc ggccacccca accttctggt     720
gagagcacct ccctctttct ctcttcctgc tttctttccc tctctcttct gttttcccct     780
```

```
gtcttttctc acttttctcc tcttctctcc tctctctctc ccccatctct ccttcctctt    840
ttctctctcc ctccctctct ccttcctctt ctctttctct ctcattttca ctgtcatatg    900
tttcttcctt ttatcttcct ctcatcctct gtctacatat tatttaagat tttttaccaa    960
aagtgaatca ccaaatgaaa aggatgtgtg ctagggtcag attctgcctt attttcttct   1020
taagccctcc ctctgatcat gtgcaactgt agatcacatt gaagatgtga aaaactgtaa   1080
gccattt                                                             1087
```

<210> SEQ ID NO 28
<211> LENGTH: 667
<212> TYPE: DNA
<213> ORGANISM: Homo sapiens

<400> SEQUENCE: 28

```
tgttttcaac tttctctttt attcctttgc acttttttttt gagacagggt ctcactctgt     60
cacccaggct agagtgcagt agtgcaaaca cagctcactg cagcctcaat tctctcgagc    120
tcaagcgatc ctcccatctc agcctcccga gtaagtagct gggactacag gtgcgtatca    180
ccatgcccag ctaattttgg tatttttttt ttttagagac aggatttcac catgttgccc    240
aggctggtct caaactcctg agctcaagca atccacctgc tcaacctcc caaagtgcca    300 agattacaga cgtgagccac tgcccctggc cttctttgca tattttaaac atagttattt    360
atattctcta ttaggtaccc aataactgag gtcactaggg gtttagttct tccacctgtt    420
ttttttctag ctcttgttca tagggctttt ccctcatttg ttttgtaatt ttgtataaaa    480
agctcttttc tccctgtctt gatctcacac ctacattgga acatttccaa tctagaatag    540
tttaagttaa cttctggtcc aagctggtag tataatttca tatccatgca tgtagtatga    600
aaacaggatt gtggttatga gttctcaaga aagcctcttt ttctgcaccc agaggcgagg    660
caaggaa                                                             667
```

<210> SEQ ID NO 29
<211> LENGTH: 799
<212> TYPE: DNA
<213> ORGANISM: Homo sapiens

<400> SEQUENCE: 29

```
tgctgcaggc acatgggggt catctctggc tggcaggaag gtgagggagt cctctcttct     60
ctggtcctgg ctgactctgc ctcagcagga cttcacttga ccattctcac cttctgtcac    120
ctcatcctta aagtgacaga gtaaattaac tctaaggccc catccaggac tcaagctgtg    180
tgattttaca aaaatgaaaa ttatattaat aatcccattg taaatcccaa aagaaagtc    240 aagagactag cagaaagaca ggtgggtgat gggatgtcct ggacagagcc tggatcatga    300
ggtccccatg tagtgcttgt actacgcaga tgtttcctct tgagctattt taaaggtgtg    360
gaaaaagcca agcaatgcc ctctccacgg atactaaaga ctcacctttc cactcagctg    420
ctgccaccgt ctttctggga aaacaactgc aaggtaagat accaacagct ccctgtgaca    480
gaagggaaag taagccaacc aaagcgagtc ctgcagaccc aacgcagag cattcgtgat    540 cacctttgcc tctccactgt ctctgatgct taccagcaaa gagaaaacat aaagttctac    600
attcagcagg acattcacct gaacagtttc aaataggaca tgaaggcagg atccagattg    660
aatgtttgga gggaactaga gacatgggga ggcagtgagt gcagtaagcg tagctgtgaa    720
atgaagggga gaagatggtg gtcccaggct gcaggccatg gggaggtttt ctaacagacc    780
```

```
aggggagggaa gaatgagag                                                    799
```

<210> SEQ ID NO 30
<211> LENGTH: 1304
<212> TYPE: DNA
<213> ORGANISM: Homo sapiens

<400> SEQUENCE: 30

```
aagtccactt tttataccat cttttaccca cctctttcct taccccaaag ttcctttatg    60
tagctcgaaa tgccaaagac tgtatggttt cctactacca tttccaaagg atgaaccaca   120
tgcttcctga ccctggtacc tgggaagagt attttgaaac cttcatcaat ggaaaaggta   180
cgggaacatc cttcacaccc ttgcattctc actccagcta ggctgggtct agggaaccac   240
aggcagcatt ttatccccta gaatgcctgt acttcatcag gtgtgtccta ccacagactg   300
ggactgggca gagcaagctg gccactgagt gtatgcccac agccctcagc aaacatcttc   360
cacctgattc agagtcttta attacagcca tcctcttcca aaaggtgtcc ttgtccctat   420
gtgattgcac ataataggaa gccactttag ggacgatgtt ggggcaagta accctaaggc   480
tgtccccatc tacaccaccc tcaaaatcaa acagatcaga acccttagga catatctaat   540
acagaatttg gttttctct ctctaactca cttcaggaaa atccctaata ctcagaaggt   600
tttgtgtgat gcctatgtag actattctgt ttcctgtgtc tatttcagtg gtttggggtt   660
cctggtttga ccacgtgaaa ggatggtggg agatgaaaga cagacaccag attctcttcc   720
tcttctatga ggacataaag agggtgagtg aaggctctgc agaagaacca ttttaaagtg   780
gttcttcagg tgcagagaaa ttcaaagttg tttcaaagga catcccagag aattgtagta   840
tttcttatg atactctcat tcattccagt ccaatgttac ccttgccgca ggacccaaag   900
catgaaattc ggaaggtgat gcagttcatg ggaaagaagg tggatgaaac agtgctagat   960
aaaattgtcc aggagacgtc atttgagaaa atgaaagaaa atcccatgac aaatcgttct  1020
acagtttcca atctatcttt ggaccagtca atttcctcct tcatgagaaa aggtgtgtgg  1080
ggcctctttta tcatacattc agattgtctc gtaacatcct gtctgcctct tagcagacaa  1140
tattgagttt tattaattcc aagccaatgc atttcaacta ttcctaatat gtgtttctaa  1200
taaaaccagg gatttgatcc tgttgtagaa gagagctttc tagggtattg ttccagtatt  1260
tggttgcaag gaacagagag tccctcaagc tagccccaaa gaaa                    1304
```

<210> SEQ ID NO 31
<211> LENGTH: 1080
<212> TYPE: DNA
<213> ORGANISM: Homo sapiens

<400> SEQUENCE: 31

```
ttgctcaaca taatgttttg agattcctcc atgtggttgt gtgtctgtag ttcatcattc    60
ttttatgtct atgtagtaat ccatcaggta aatacactac aggtgggggcc aggtcatgca   120
ggccactagc tgccttgggt cagttgtcca gctgacttag aagtccatcc ccctgcacag   180
agtcccctag gcctgcttct tataggagag ctgctcatgg acaggtgtcc actgaagggg   240
gagttgggtg agtcaggtat gtggacaggc cagattcagt atgggcacta caccactta   300
ctcagggaca ccacatcttt caatcagagt gacactcctg tctggcctttc cttttctag   360
gaactgtggg ggattggaaa aaccacttca ctgttgccca gaatgagagg tttgatgaaa   420
tctatagaag aaagatgaa ggaacctcca taaacttctg catggaactc tgagcaagat   480
gtaaatataaaa ttaaaaggtg gatggcaaga gtgcaaatac tatcttcaat ccttcagtcc   540
```

```
cagccagaag aatctctgaa agcatattgt gaatgtatac aatgtagtac aaacaatctc      600
tgtgatgatt aacagtatgt caccacttca ttttttaaaa aggatcacgt ctaatgccca      660
ttttcccaac tattctttcc aaagtaagat ataaggtagc ttaataaact aagtaaaacg      720
tatgacttga gtacaaaagg attgttttaa tccccattat tctggaaagt gcatcctagt      780
ctcccagtct ataacatcat aataccttga gtataagtcc aaatattagg ttatatctat      840
attaaaaaca aaatttctgt catctgtcct ggccattcag gcaactccag cctgggctca      900
atcctggagt tctgtctggt cactatcaga aggaacactt tgagggaaac cctggtgcag      960
ccagccctga ggaaacatgg cctgagtgcc ctcactggtg ggtgggaata aaatggaagt     1020
gcacagagga gatgtcagaa gaccaaaact tggtgaatag tcccagtgct aggtcatata     1080
```

<210> SEQ ID NO 32
<211> LENGTH: 1380
<212> TYPE: DNA
<213> ORGANISM: Homo sapiens

<400> SEQUENCE: 32

```
tacaggagag agagcttttg gaggtgattt gaggggggtc ctgaatttct aggtctgaat       60
ttttaggctg gaggctgtta acaaaactct tttatattat tttatcagat tcttaggatc      120
ttttctggtt tgaataaatg catctgtaaa gccacaccta tgtggctaaa ggttaaaaaa      180
taaattaacg agttaggtac agaatttctt ttaagccata ttcttacctt caagttccag      240
ctgaaagtca gcagctcaaa gcccactcaa gggtcagtg gcacggaaa ggactttcac       300 aggaagcaga cggcaattgc agaggctcaa attactactg tgtcagagtt acggggcgc       360 tcagcaggta gccagcactt tgggaggctc tcagcttcag tgtgggaagt tgaagctttt      420
actggaagaa tccggattga acagaaacaa accctgtgac ctggccctgg agggagaac       480 ttctcactgt accatgatca ctcatgtgac cctgactgct gtgcaaatac caactccctc      540
tagttcatat gaactaaggg cacactctac tcctcctctc ggtcaccagc tagagttttt      600
cacatctttc ctggccctca gctgcctggc ccctccctcc tcccactggc ctcgaagctt      660
aaacaggtgg gggctggggg gaaatggaag gttggctcta ggaccagatg catcaggctt      720
caggtaggct cctgcttatt tggtgaactc ccttttcctt cctccttagc ctgagattta      780
atttctgcat ctatgaagtg tgggtaatac tgcctgtctc caatccatgc tttaagattg      840
aaagcaacaa tgttgatgaa tacactttgc agagcaaata gtaagtgctt aaaactgctg      900
gttcttcttt cctttcttcc caagttgtat tcatccacac cgaaaatgca gagaggatag      960
aacaaaagtc tagagcttag gtgtgtactt atttttttctt tgccttattg tacaaaaggt     1020
acactttagt ggaggcagat tatattccat ggtgtctttg gttacctggg aaattaaatg     1080
gatcaagtgt taatgatctc tgaactgcta ctcttctgcc agccccaacc ttgtatctac     1140
cccagtgctt tcctttctgg aattgaagca taattctgca cccatctgc ccttcttgcc      1200 aaagctttcc ttgtcttctt tgaccctgaa cctcctaatg cttctttgcc gacacttctt     1260
cttcctcctt gtttccaaag ggctcttttt ttcccaataa attgaacttt cttttcttt      1320 cttttttctt ttttttttt tttttgaga tggtgtttca ctcctgttgc ccaggctgga     1380
```

<210> SEQ ID NO 33
<211> LENGTH: 1086
<212> TYPE: DNA
<213> ORGANISM: Homo sapiens

```
<400> SEQUENCE: 33
aaatggctta cagttttca catcttcaat gtgatctaca gttgcacatg atcagaggga     60
gggcttaaga agaaaataag gcagaatctg accctagcac acatccttt catttggtga   120 ttcacttttg gtaaaaaatc ttaaataata tgtagacaga ggatgagagg aagataaaag   180
gaagaaacat atgacagtga aaatgagaga gaaagagaag aggaaggaga gagggaggga   240
gagagaaaag aggaaggaga gatggggag agagagagga gagaagagga gaaaagtgag   300
aaaagacagg ggaaaacaga agagagaggg aaagaaagca ggaagagaga aagagggagg   360
tgctctcacc agaaggttgg ggtggccgag cccactcaat gaaaggatgg cggtgttgga   420
tgatggctcg ctggcacttc tccacgtccc cattctgttc aatcatatcc acaatttcct   480
gaatccacgt tgtccctgag gctcagaaag gaaggatgaa agcagaaat ctgttagaca   540 atcttccctg aagagtcccg agtaaacgaa gaggatgtag agccttggtg tttgcatcac   600 cctcccttg ggtcagaatc ctgtttgcca tgagtgatag aagtccatga gggatggact   660
ttggatctct gtagggagtg gagcagcaca ggcaagggtc tctccaccca agaccagtgc   720
atggtagagc atagcagctt tcctggaaaa ctcggatatc aggcatcctg tgtgagccct   780
gagctccaaa acccattgtg gaacaataag aaggagcagg tttcctaaga aggggaattc   840
taacttaagt gatgagcctg tgctggctca gcaggtcttt gctgtccctc ctaccctgca   900
atcacctgct ttagggtagg tgcagatgag gagatcatct ggtttggcct cgaagctctg   960
gatctggctc cagttgtcca cagttgcagg ctgcaggagg gtcccctcca cctcttcag  1020 tttatctgt ttccccaggt ctgaggtcag ggccatagtg tctcagggtt ggggtcccta  1080
tgggaa                                                              1086

<210> SEQ ID NO 34
<211> LENGTH: 667
<212> TYPE: DNA
<213> ORGANISM: Homo sapiens

<400> SEQUENCE: 34
ttccttgcct cgcctctggg tgcagaaaaa gaggctttct tgagaactca taaccacaat    60
cctgttttca tactacatgc atggatatga aattatacta ccagcttgga ccagaagtta   120
acttaaacta ttctagattg gaaatgttcc aatgtaggtg tgagatcaag acagggagaa   180
aagagctttt tatacaaaat tacaaaacaa atgagggaaa agccctatga acaagagcta   240
gaaaaaaaac aggtggaaga actaaacccc tagtgacctc agttattggg tacctaatag   300
agaatataaa taactatgtt taaaatatgc aaagaaggcc aggggcagtg gctcacgtct   360
gtaatcttgg cactttggga ggttgaggca ggtggattgc ttgagctcag gagtttgaga   420
ccagcctggg caacatggtg aaatcctgtc tctaaaaaaa aaaatacca aaattagctg   480 ggcatggtga tacgcacctg tagtcccagc tacttactcg ggaggctgag atgggaggat   540
cgcttgagct cgagagaatt gaggctgcag tgagctgtgt ttgcactact gcactctagc   600
ctgggtgaca gagtgagacc ctgtctcaaa aaaaagtgca aaggaataaa agagaaagtt   660
gaaaaca                                                             667

<210> SEQ ID NO 35
<211> LENGTH: 799
<212> TYPE: DNA
<213> ORGANISM: Homo sapiens

<400> SEQUENCE: 35
```

```
ctctcattct tccctccctg gtctgttaga aaacctcccc atggcctgca gcctgggacc    60
accatcttct cccttcatt tcacagctac gcttactgca ctcactgcct ccccatgtct   120
ctagttccct ccaaacattc aatctggatc ctgccttcat gtcctatttg aaactgttca   180
ggtgaatgtc ctgctgaatg tagaaccttta tgttttctct ttgctggtaa gcatcagaga   240
cagtggagag gcaaaggtga tcacgaatgc tctgcgttgg ggtctgcagg actcgctttg   300
gttggcttac tttcccttct gtcacaggga gctgttggta tcttaccttg cagttgtttt   360
cccagaaaga cggtggcagc agctgagtgg aaaggtgagt ctttagtatc cgtggagagg   420
gcattgcttt ggcttttttcc acacctttaa aatagctcaa gaggaaacat ctgcgtagta   480
caagcactac atggggacct catgatccag gctctgtcca ggacatccca tcacccacct   540
gtctttctgc tagtctcttg actttctttt gggattttac aatgggatta ttaatataat   600
tttcattttt gtaaaatcac acagcttgag tcctggatgg ggccttagag ttaatttact   660
ctgtcacttt aaggatgagg tgacagaagg tgagaatggt caagtgaagt cctgctgagg   720
cagagtcagc caggaccaga gaagagagga ctccctcacc ttcctgccag ccagagatga   780
cccccatgtg cctgcagca                                              799

<210> SEQ ID NO 36
<211> LENGTH: 1304
<212> TYPE: DNA
<213> ORGANISM: Homo sapiens

<400> SEQUENCE: 36
tttctttggg gctagcttga gggactctct gttccttgca accaaatact ggaacaatac    60
cctagaaagc tctcttctac aacaggatca atccctggt tttattagaa acacatatta   120
ggaatagttg aaatgcattg gcttggaatt aataaaactc aatattgtct gctaagaggc   180
agacaggatg ttacgagaca atctgaatgt atgataaaga ggcccacac accttttctc   240 atgaaggagg aaattgactg gtccaagata gatttggaaa ctgtagaacg atttgtcatg   300
ggattttctt tcatttctc aaatgacgtc tcctggacaa ttttatctag cactgtttca   360
tccaccttct ttcccatgaa ctgcatcacc ttccgaattt catgctttgg gtcctgcggc   420
aagggtaaca ttggactgga atgaatgaga gtatcataaa gaaatactac aattctctgg   480
gatgtccttt gaacaacttt tgaatttctc tgcacctgaa gaaccacttt aaaatggttc   540
ttctgcagag ccttcactca ccctctttat gtcctcatag aagaggaaga gaatctggtg   600
tctgtctttc atctcccacc atcctttcac gtggtcaaac caggaacccc aaaccactga   660
aatagacaca ggaaacagaa tagtctacat aggcatcaca caaaaccttc tgagtattag   720 ggatttttcct gaagtgagtt agagagagaa acccaaaatt ctgtattaga tatgtcctaa   780
gggttctgat ctgtttgatt ttgagggtgg tgtagatggg gacagcctta gggttacttg   840
ccccaacatc gtccctaaag tggcttccta ttatgtgcaa tcacataggg acaaggacac   900
cttttggaag aggatggctg taattaaaga ctctgaatca ggtggaagat gtttgctgag   960
ggctgtgggc atacactcag tggccagctt gctctgccca gtcccagtct gtggtaggac  1020
acacctgatg aagtacaggc attctagggg ataaaatgct gcctgtggtt ccctagaccc  1080
agcctagctg gagtgagaat gcaagggtgt gaaggatgtt cccgtacctt ttccattgat  1140
gaaggtttca aaatactctt cccaggtacc agggtcagga agcatgtggt tcatcctttg  1200
gaaatggtag taggaaacca tacagtcttt ggcatttcga gctacataaa ggaactttgg  1260
```

-continued

```
ggtaagaaaa gaggtgggta aaagatggta taaaaagtgg actt            1304
```

<210> SEQ ID NO 37
<211> LENGTH: 1080
<212> TYPE: DNA
<213> ORGANISM: Homo sapiens

<400> SEQUENCE: 37

```
tatatgacct agcactggga ctattcacca agttttggtc ttctgacatc tcctctgtgc     60
acttccattt tattcccacc caccagtgag ggcactcagg ccatgtttcc tcagggctgg    120
ctgcaccagg gtttccctca aagtgttcct tctgatagtg accagacaga actccaggat    180
tgagcccagg ctggagttgc ctgaatggcc aggacagatg acagaaattt tgtttttaat    240
atagatataa cctaatattt ggacttatac tcaaggtatt atgatgttat agactgggag    300
actaggatgc actttccaga ataatgggga ttaaaacaat cctttttgtac tcaagtcata    360 cgttttactt agtttattaa gctaccttat atcttacttt ggaaagaata gttgggaaaa    420
tgggcattag acgtgatcct ttttaaaaaa tgaagtggtg acatactgtt aatcatcaca    480
gagattgttt gtactacatt gtatacattc acaatatgct ttcagagatt cttctggctg    540
ggactgaagg attgaagata gtatttgcac tcttgccatc caccttttaa ttttatttac    600
atcttgctca gagttccatg cagaagttta tggaggttcc ttccatcttt cttctataga    660
tttcatcaaa cctctcattc tgggcaacag tgaagtggtt tttccaatcc cccacagttc    720
ctagaaaaag gaaggccaga caggagtgtc actctgattg aaagatgtgg tgtccctgag    780
taaagtggtg tagtgcccat actgaatctg gcctgtccac atacctgact cacccaactc    840 cccctttcagt ggacacctgt ccatgagcag ctctcctata agaagcaggc ctagggggact    900 ctgtgcaggg ggatggactt ctaagtcagc tggacaactg acccaaggca gctagtggcc    960
tgcatgacct ggccccacct gtagtgtatt tacctgatgg attactacat agacataaaa   1020
gaatgatgaa ctacagacac acaaccacat ggaggaatct caaaacatta tgttgagcaa   1080
```